(12) United States Patent
Zhu et al.

(10) Patent No.: US 12,390,512 B2
(45) Date of Patent: Aug. 19, 2025

(54) **DEPOLYMERASE CAPABLE OF DEGRADING EXTRACELLULAR POLYMERIC SUBSTANCES OF *KLEBSIELLA PNEUMONIAE***

(71) Applicant: SHANGHAI REINOVAX BIOLOGICS CO., LTD, Shanghai (CN)

(72) Inventors: Jeff Xianchao Zhu, Shanghai (CN); Ping He, Shanghai (CN); Yunqiang Wu, Shanghai (CN); Jiayin Li, Shanghai (CN); Juan Du, Shanghai (CN)

(73) Assignee: SHANGHAI REINOVAX BIOLOGICS CO., LTD, Shanghai (CN)

( * ) Notice: Subject to any disclaimer, the term of this patent is extended or adjusted under 35 U.S.C. 154(b) by 768 days.

(21) Appl. No.: 17/609,975

(22) PCT Filed: Apr. 23, 2020

(86) PCT No.: PCT/CN2020/086496
§ 371 (c)(1),
(2) Date: Nov. 9, 2021

(87) PCT Pub. No.: WO2020/228508
PCT Pub. Date: Nov. 19, 2020

(65) Prior Publication Data
US 2022/0202917 A1    Jun. 30, 2022

(30) Foreign Application Priority Data

May 10, 2019  (CN) .................. 2019 10388278.3
Apr. 20, 2020  (CN) .................. 2020 10312073.X

(51) Int. Cl.
| | | |
|---|---|---|
| *A61K 38/47* | (2006.01) | |
| *A61K 45/06* | (2006.01) | |
| *A61P 31/04* | (2006.01) | |

(52) U.S. Cl.
CPC .............. *A61K 38/47* (2013.01); *A61K 45/06* (2013.01); *A61P 31/04* (2018.01)

(58) Field of Classification Search
None
See application file for complete search history.

(56) References Cited

FOREIGN PATENT DOCUMENTS

| | | | |
|---|---|---|---|
| CN | 109536459 A | 3/2019 | |
| CN | 110079508 A | 8/2019 | |
| WO | WO-2010141135 A2 * | 12/2010 | .............. A61K 35/76 |

OTHER PUBLICATIONS

UniProt A0A0U3C9T3, Depolymerase 1, capsule K47-specific, amino acid sequence, 2016 (Year: 2016).*

(Continued)

*Primary Examiner* — Louise W Humphrey
*Assistant Examiner* — Mary A Crum
(74) *Attorney, Agent, or Firm* — Merchant & Gould P.C.; Daniel J. Pereira

(57) ABSTRACT

A depolymerase may be capable of degrading extracellular polymeric substances of *Klebsiella pneumoniae* capsular type K47. The depolymerase can degrade extracellular polymeric substances of *Klebsiella pneumoniae*. Such a depolymerase may be a) an enzyme having a sequence as set forth in SEQ ID NO: 1, or having at least 80% homology thereto and having an activity of degrading extracellular polymeric substances from K47 capsular *Klebsiella pneumoniae*; and/or b) an enzyme having a sequence as set forth in SEQ ID NO: 2, or having at least 80% homology thereto and having (Continued)

an activity of degrading extracellular polymeric substances from K47 capsular *Klebsiella pneumoniae*.

20 Claims, 9 Drawing Sheets

Specification includes a Sequence Listing.

(56) References Cited

OTHER PUBLICATIONS

UniProt A0A0U3DL17, Depolymerase 1, capsule K47-specific, amino acid sequence, 2016 (Year: 2016).*

Ju, Zhigang, et al. "Drug delivery vectors based on filamentous bacteriophages and phage-mimetic nanoparticles." Drug Delivery 24.1 (2017): 1898-1908 (Year: 2017).*

Appendix A, sequence alignment, 2024 (Year: 2024).*

NCBI Taxonomy Browser, Klebsiella phage vB_KpnP_IME205, 2020 (Year: 2020).*

Del Bono, Valerio, et al. "Meropenem for treating KPC-producing Klebsiella pneumoniae bloodstream infections: should we get to the PK/PD root of the paradox?." Virulence 8.1 (2017): 66-73 (Year: 2017).*

GenBank KU183006.1, Klebsiella phage vB_KpnP_IME205, complete genome, 2015 (Year: 2015).*

UniProt A0A0U3C9T3, Depolymerase1, capsule K47-specific, from Klebsiella phage vB_KpnP_IME205, 2025 (Year: 2025).*

Appendix B, Seq Id No. 2 and ALT58498.1 sequence alignment, 2025 (Year: 2025).*

International Search Report issued on Jul. 16, 2020 in PCT/CN2020/086496 filed Apr. 23, 2020, 3 pages.

Wu, Y., et al., "GenBank Accession No. QDF14645, Version QDF14645. 1, Oct. 31, 2019", GenBank, 2019, 1 total page.

Yannan, L., et al., "Identification of Two Depolymerases From Phage IME205 and Their Antivirulent Functions on K47 Capsule of Klebsiella pneumoniae", Frontiers in Microbiology, vol. 11, 2020, pp. 1-11.

* cited by examiner

1. Bacteriophage
2. SUMO protein
3. PBS
4. Dpo42 depolymerase
5. Dpo43 depolymerase

DEPOLYMERASE CAPABLE OF DEGRADING EXTRACELLULAR POLYMERIC SUBSTANCES OF *KLEBSIELLA PNEUMONIAE*

CROSS-REFERENCE TO RELATED APPLICATIONS

This application the national stage of international application PCT/CN2020/086496, filed on Apr. 23, 2020, and claims the priority of Chinese Patent Application No. 201910388278.3, filed 10 May 2019, titled "bacteriophage, bacteriophage-expressed depolymerase and preparation method and application thereof"; and Chinese Patent Application No. 202010312073.X, filed 20 Apr. 2020, titled "pharmaceutical composition comprising a depolymerase capable of degrading extracellular polymeric substances from *Klebsiella pneumoniae*", the disclosure of which are incorporated herein by reference.

In accordance with 37 CFR § 1.52 (e) (5) and with 37 CFR § 1.831, the specification makes reference to a Sequence Listing submitted electronically as a.txt file named 534279US_ST25.txt. Said.txt copy, created on Nov. 9, 2021 and filed is 18,000 bytes in size. The entire contents of the Sequence Listing are hereby incorporated by reference.

TECHNICAL FIELD

The present disclosure relates to the field of biomedicine, particularly relates to a depolymerase capable of degrading extracellular polymeric substances of *Klebsiella pneumoniae*.

BACKGROUND OF THE INVENTION

In recent years, antibiotic resistance has become an increasingly serious problem. Especially the generation of bacterial biofilm, which increases the resistance of bacteria to antibiotics by 10 to 1000 times, poses a great challenge to clinical treatment. It is estimated by the experts from U.S. Centers for Disease Control and Prevention that 65% infection in human are related to infection by biofilm-secreting bacterium. The pathogenicity of bacterium depends on the ability of bacteria to form a biofilm, and bacterial biofilm formation is also a very important process in infection. Bacteriophage is a general virus that can infect microorganisms such as bacteria, fungi, actinomycetes, spirochetes, etc, which are called bacteriophage since some of them may cause the lysis of host bacteria. Bacteriophage can provide us with a natural, highly specific and non-toxic way to prevent and control bacterial biofilms.

*Klebsiella pneumoniae* is a pathogenic gram-negative bacillus with important clinical research value, which can normally be colonized in parts, such as mouth, skin, and intestines, etc, but it can also cause serious hospital and out-of-hospital infections including community-acquired pneumonia, liver abscess, respiratory tract infection, and sepsis, etc. In recent years, *Klebsiella pneumoniae* has become an important pathogen of iatrogenic infections due to the abuse of antibiotics.

The *Klebsiella pneumoniae* strains that produce extended-spectrum β-lactamases (ESBLs) and carbapenemases have increased significantly in number in the past few decades (these two enzymes are multi-drug resistant) and have been listed by the U.S. Centers for Disease Control (CDC) as an imminent threat to public health. Polysaccharide is one of the most important pathogenic factors of *Klebsiella pneumoniae*, which can form capsular polysaccharide (CPS) around the cell or be released as exopolysaccharide (EPS). Capsular polysaccharides play an important role in the infection and invasion of *Klebsiella pneumoniae*, including resisting host defense mechanisms, inhibiting early inflammatory reaction, preventing the entry of bacteriophage, assisting bacterial adhesion and promoting the formation of biofilm.

*Klebsiella pneumoniae* has the ability of synthesizing and secreting EPS, which may lead to the formation of natural biofilms. The ability of biofilm formation also defines the pathogenicity of bacteria, which is of great significance during infection. Biofilm is a colony of bacterial cells attached to a special surface, embedded in a matrix composed of extracellular polymeric substances (EPS). The EPS matrix is mainly composed of proteins, nucleic acids, polysaccharides and lipids. The formation of biofilm on the surface of the catheter allows bacteria to protect themselves from adverse environmental factors (such as drying, detergents and host immune defense attacks) and the penetration of antibiotics. It has been reported that once a strain forms a biofilm structure, its resistance rate to antibacterial drugs can be increased by 10 to 1000 times. Therefore, there is an urgent need to find alternative strategies against the development of biofilms.

In view of this, the present disclosure is proposed.

SUMMARY OF THE INVENTION

A first aspect of the present disclosure is to provide a depolymerase selected from:
a) an enzyme having a sequence represented by SEQ ID NO: 1, or having at least 80% homology thereto and having an activity of degrading extracellular polymeric substances from K47 capsular *Klebsiella pneumoniae*;
b) an enzyme having a sequence represented by SEQ ID NO: 2, or having at least 80% homology thereto and having an activity of degrading extracellular polymeric substances from K47 capsular *Klebsiella pneumoniae*.

A second aspect of the present disclosure is to provide a nucleic acid encoding the depolymerase as described above. The present disclosure also includes a vector comprising the nucleic acid.

A third aspect of the present disclosure is to provide a host cell comprising the nucleic acid as described above, and/or the vector as described above.

A fourth aspect of the present disclosure is to provide a *Klebsiella pneumoniae* bacteriophage capable of expressing the depolymerase as described above.

A fifth aspect of the present disclosure is to provide a method of preparing a depolymerase, comprising:
1) incubating the host cell of claim 11, 2) expressing the depolymerase, 3) isolating the depolymerase from the host cell;
or;
1') incubating the *Klebsiella pneumoniae* bacteriophage of claim 12 or 13 using K47 capsular *Klebsiella pneumoniae* as a substrate, 2') lysing the K47 capsular *Klebsiella pneumoniae* bacteriophage and isolating the depolymerase.

A sixth aspect of the present disclosure is to provide a pharmaceutical composition, comprising:
i) the depolymerase as described above, or the *Klebsiella pneumoniae* bacteriophage as described above; and
ii) any one or a combination of at least two of optional pharmaceutically acceptable carriers, excipients or diluents.

A seventh aspect of the present disclosure is to provide a method of treating diseases caused by *Klebsiella pneumoniae*, the method comprises steps of administering to a host an effective amount of the pharmaceutical composition as described above.

The present disclosure has the following beneficial effects:

the present disclosure provides a depolymerase capable of effectively decomposing the extracellular polymeric substances from *Klebsiella pneumoniae*, thereby facilitating the contact of the drug capable of killing the bacterium with the bacterium to bring it into play.

BRIEF DESCRIPTION OF THE DRAWING

To describe the technical solutions of the embodiments of the present disclosure or the prior art more clearly, the following briefly introduces the accompanying drawings required for describing the embodiments or the prior art. Apparently, the accompanying drawings in the following description show some embodiments of the present disclosure, and persons of ordinary skill in the art may also derive other drawings from these accompanying drawings without creative efforts.

Figure 1:
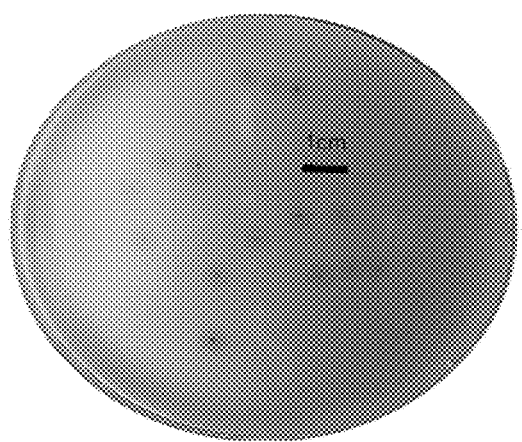
FIG. 1 shows the bacteriophage plaque and halo formed by the bacteriophage SH-KP152302 on a Kp2302 double-layer agar plate according to an embodiment of the present disclosure.

The *Klebsiella pneumoniae* bacteriophage strain, provided by the present application, is named SH-KP152302, deposited at the Guangdong Microbial Culture Collection Center, with the deposit address of which is Guangdong Institute of Microbiology, 5th Floor, Building 59, Courtyard No. 100, Xianlie Middle Road, Guangzhou, with the deposit number of GDMCC No: 60968. the strain was received by the collection center on Feb. 24, 2020 and be made entries in a register; and it was tested as a viable strain by the collection center on Feb. 25, 2020.

DETAILED DESCRIPTION

Reference to the embodiments of the present disclosure will now be provided in detail, one or more examples of which are described below. Each example is provided as an explanation rather than a limitation of the present disclosure. In fact, it is apparently to those skilled in the art that various modifications and changes may be made to the present disclosure without departing from the scope or spirit of the present disclosure. For example, features illustrated or described as part of one embodiment may be used in another embodiment to produce a further embodiment.

Such modifications and changes falling within the scope of the appended claims and the scope of equivalency of the claims are therefore intended to be embraced in the present disclosure. Other objects, features and aspects of the present disclosure are disclosed in or are apparent from the following detailed description. It should be understood by those of ordinary skill in the art that the present discussion is only a description of exemplary embodiments and is not intended to limit the broader aspects of the present disclosure.

The present disclosure relates to a depolymerase selected from:

a) an enzyme having a sequence represented by SEQ ID NO: 1, or having at least 80% homology thereto and having an activity of degrading extracellular polymeric substances from K47 capsular *Klebsiella pneumoniae*; or b) an enzyme having a sequence represented by SEQ ID NO: 2, or having at least 80% homology thereto and having an activity of degrading extracellular polymeric substances from K47 capsular *Klebsiella pneumoniae*.

For ease of presentation, the depolymerases represented by SEQ ID NO: 1 and 2 are referred to as "Dpo42" and "Dpo43" respectively hereafter. In the present disclosure, the K47 capsular *Klebsiella pneumoniae* means *Klebsiella pneumoniae* which is determined to be the K47 capsular type according to the wzi classification method.

This enzyme can specifically degrade the extracellular capsular polysaccharide of *Klebsiella pneumoniae*, not only can inhibit the formation of *Klebsiella pneumoniae* biofilm, but also can remove the biofilm to a certain extent, and exhibits a dose-dependent activity in the process preventing the biofilm formation.

Alternatively, the depolymerase may be an enzyme having at least 81%, 82%, 83%, 84%, 85%, 86%, 87%, 88%, 89%, 90%, 91%, 92%, 93%, 94%, 95%, 96%, 97%, 98%, 99%, 99.5% homology to the full-length sequence represented by SEQ ID NO: 1 or 2 and having the activity of degrading the extracellular polymeric substances from *Klebsiella pneumonia*.

In addition, in view of that the present application further limits that the depolymerase has the activity of degrading the extracellular polymeric substances from *Klebsiella pneumoniae*, it is therefore easy for those skilled in the art to think of modifying protein sequence by conservative substitution only in the conserved region of the sequence represented by SEQ ID NO: 1 or 2 to obtain substantially similar sequences. Preferably, substantially similar sequences also keep the unique activity of the polypeptide. The substitutions generally regarded as conservative substitutions are the substitution between any two of the aliphatic amino acids Ala, Val, Leu, and Ile, the substitution between hydroxyl residues Ser and Thr, the substitution between acidic residues Asp and Glu, the substitution between amide residues Asn and Gln, the substitution between the basic residues Lys and Arg, or the substitution between the aromatic residues Phe and Tyr.

In the present disclosure, "having an activity of degrading the extracellular polymeric substances from *Klebsiella pneumoniae*" or "having a depolymerase activity" may be understood as having at least 40%, 50%, 60%, 70%, 80%, 90% % or 95% of degradation for the extracellular polymeric substances from *Klebsiella pneumoniae*. This percentage is obtained by comparing with the data measured under an optimal transcriptase hydrolysis condition for the wild type.

In the present disclosure, "extracellular polymer" may be used interchangeably with terms such as "extracellular polymeric substance" and "extracellular capsular polysaccharide". Extracellular polymeric substance may be some high-molecular polymer secreted in vitro by microorganisms, mainly bacteria, under certain environmental conditions. Extracellular polymeric substance has main components which are similar to the intracellular components of microorganisms, and are macromolecular substances, such as polymers, for example, polysaccharides, proteins and nucleic acids.

In some embodiments, the depolymerase is derived from *Klebsiella pneumoniae* bacteriophage.

In some embodiments, the *Klebsiella pneumoniae* bacteriophage is deposited with the deposit number of GDMCC No: 60968.

In some embodiments, the depolymerase in a) has a depolymerase activity at pH5-9.

In some embodiments, the depolymerase in a) has a depolymerase activity between 25° C. and 80° C.

In some embodiments, the depolymerase in b) has a depolymerase activity at pH4-10.

In some embodiments, the depolymerase in b) has an optimal reaction pH of about 7, for example, 6-8.

In some embodiments, the depolymerase in b) has a depolymerase activity between 25° C. and 70° C.

In some embodiments, the depolymerase in b) has an optimal reaction temperature at about 25° C., for example, 23° C. ~27° C.

According to a further aspect of the present disclosure, the present disclosure also relates to a nucleic acid encoding a depolymerase as described above.

The nucleic acid may be DNA or RNA.

In some embodiments, the nucleic acid has a nucleotide sequence represented by SEQ ID NO: 3 or 4.

The nucleotide sequence represented by SEQ ID NO: 3 or 4 corresponds to the amino acid sequence represented by SEQ ID NO: 1 or 2, respectively.

The present disclosure also relates to a vector comprising a vector of nucleic acid as described above.

The term "vector" refers to a nucleic acid vehicle into which polynucleotides may be inserted. The vector is called an expression vector when it can express the protein encoded by the inserted polynucleotide. The vector may be introduced into a host cell through transformation, transduction or transfection, so that the genetic material element it carries is expressed in the host cell. Vectors are well known to those skilled in the art, including but not limited to: plasmids; phagemids; cosmids; artificial chromosomes, such as yeast artificial chromosomes (YACs), bacterial artificial chromosomes (BACs) or P1 derived artificial chromosomes (PACs); bacteriophages, such as λ bacteriophage or M13 bacteriophage and animal viruses, etc. The animal viruses that may be used as vectors include, but are not limited to: retroviruses (including lentiviruses), adenoviruses, adeno-associated viruses, herpes viruses (such as herpes simplex virus), poxviruses, baculoviruses, papillomaviruses, and papovaviruses (such as SV40). In some embodiments, the vector of the present disclosure comprises regulatory elements, such as enhancers, promoters, internal ribosome entry sites (IRES), and other expression control elements (such as transcription termination signals, or polyadenylation signal and poly (U) sequence, etc.) commonly used in genetic engineering.

The present disclosure further relates to a host cell, which comprises the nucleic acid sequences as described above, and/or the vectors as described above.

The term "host cell" refers to cells that may be used to introduce vectors, including but not limited to: prokaryotic cells, such as *Escherichia coli* (*E. coli*) or *Bacterium subtilis*, etc; fungal cells, such as yeast cells or *Aspergillus*, etc; insect cells, such as S2 drosophila cells or Sf9, etc; or animal cells, such as fibroblasts, CHO cells, COS cells, NSO cells, HeLa cells, BHK cells, HEK 293 cells or human cells, etc. The host cell is preferably a prokaryotic cell, more preferably *Escherichia coli* cell.

The nucleic acid may be integrated into the genome of the host cell, or it may present in the form of exogenous gene, for example, a plasmid.

The present disclosure further relates to a *Klebsiella pneumoniae* bacteriophage, which is capable of expressing the depolymerase as described above.

In some embodiments, the bacteriophage simultaneously expresses the depolymerase of a) and the depolymerase of b).

In some embodiments, the *Klebsiella pneumoniae* bacteriophage is deposited with the deposit number of GDMCC No: 60968.

The present disclosure claims to protect the *Klebsiella pneumoniae* bacteriophage with the above-mentioned deposit number, as well as the variant strains having mutations or modifications within a moderate range, and being capable of expressing the depolymerase as described above, or still having a strong ability of lysing *Klebsiella pneumoniae*.

The so-called "variant strain" may be a strain obtained by inserting the nucleic acid as described above into a bacteriophage in the prior art through a well-known gene editing technology, or mutating the bacteriophage with the deposit number GDMCC No: 60968 moderately, or fusing the bacteriophage with the deposit number GDMCC No: 60968 with other bacteriophages.

For a moderately mutated strain, it refers to a bacteriophage having a genome is highly similar to that of the SH-KP152302 strain. In the present application, the expression "moderately mutated strain" may encompass by being highly similar in genome:

Compared with the genome of SH-KP152302 strain, the bacteriophage strain has a genome comprising at most 150 mutation occurrences, preferably comprises at most 140, 130, 120, 110, 100, 90, 80, 70, 60, 50, 40, 30 or 20 mutation occurrences. The mutation occurrences are defined as SNP (single nucleotide polymorphism) or INDEL (insertion, deletion, and a combination of both). The number of mutation occurrences are determined as follows: the mutation occurrences that exist in the genome of the mutant strain are identified regarding the genome of the SH-KP152302 strain as a control, and each type of mutation occurrence (SNP or INDEL) represents one mutation occurrence (i.e, for example, insertion of a sequence containing several nucleotides is regarded as one mutation occurrence only). In this context, the genome sequence of the mutant strain of the present disclosure is defined by the number of mutation occurrences contained compared to the SH-KP152302 strain, in addition to such defined manner, it may also be additionally defined by its percentage of identity with the genome sequence of SH-KP152302 strain, wherein the percentage of identity herein represents the percentage of sequences found in the genome of one strain that are present in the genome of another strain, specifically: a) the percentage of sequences found in the genome of the SH-KP152302 strain and are present in the genome of the mutant strain, or b) the percentage of sequences found in the genome sequence of the mutant strain and present in the genome of the SH-KP152302 strain. Therefore, the percentage of identity of the of the mutant strain, which has only the insertion (one or more insertions) or the deletion (one or more deletions) that differs from the SH-KP152302 strain, has a genome having 100% identity with the SH-KP152302 strain, because the entire genome sequence of another strain is completely found in the genome of one strain. In a specific embodiment, the genome sequence of the mutant strain of the present disclosure defined by the number of mutation occurrences has at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, at least 99.92%, at least 99.94%, at least 99.96%, at least 99.98%, or at least 99.99% identity with the SH-KP152302 strain, wherein the percentage of identity represents the percentage of sequences found in the genome of one strain and present in the genome of another strain; the identity is described in terms of comparing two genome sequences over their full length (global alignment), and may be calculated using any one program based on the Needleman-Wunsch algorithm.

The present disclosure further relates to a method of preparing a depolymerase, comprising:

1) culturing the host cell as described above, 2) expressing the depolymerase, 3) isolating the depolymerase from the host cell; or;

1') culturing the *Klebsiella pneumoniae* bacteriophage as described above using K47 capsular *Klebsiella pneumoniae* as a substrate, 2') lysing the K47 capsular *Klebsiella pneumoniae* bacteriophage and isolating the depolymerase.

The present disclosure further relates to a pharmaceutical composition, comprising:

i) the depolymerase as described above, or the *Klebsiella pneumoniae* bacteriophage as described above; and ii) any one or a combination of at least two of optional pharmaceutically acceptable carriers, excipients or diluents.

The pharmaceutical composition has a broader spectrum capacity of inhibiting K47 capsular *Klebsiella pneumonia* bacteriophage.

In some embodiments, the pharmaceutical composition further comprises antibiotic drugs having a killing or inhibitory effect on *Klebsiella pneumoniae* cells.

In some embodiments, the antibiotic drug is one or more selected from the group consisting of:

ampicillin, sulbactam, piperacillin, tazobactam, cefazolin, ceftriaxone, ceftazidime, cefepime, cefoxitin, aztreonam, ciprofloxacin, levofloxacin, gentamicin, tobramycin, amikacin, polymyxin, ertapenem, imipenem, meropenem, cotrimoxazole and tigecycline.

The present disclosure further relates to a method of inhibiting or killing *Klebsiella pneumoniae*, or known as a method of treating infections caused by *Klebsiella pneumoniae*, the method comprising steps of administering to a host with an effective amount of drugs.

The embodiments of the present disclosure will be described in detail below in combination with examples.

The drug may be defined by the pharmaceutical composition as described above.

The concept of "host" usually refers to an animal infected by *Klebsiella pneumoniae*, or an organ of the animal (especially an organ related to the respiratory tract), or a cell of the animal (especially a cell derived from the respiratory tract).

The term "effective amount" described in the present disclosure refers to the dose of the component corresponding to this term that achieves the treatment, prevention, alleviation and/or relief of the disease or condition described in the present disclosure in a subject.

In the present disclosure, the term "respiratory tract" may include the following three parts:

Upper respiratory tract: nose, meatus nasi, sinuses, larynx and pharynx.

Trachea: prominentia laryngea, trachea, bronchi and secondary bronchi.

Lungs: bronchia, alveolar duct and alveoli.

Such animals are usually mammals, further primates, and further humans.

EXAMPLE 1 Dpo43 Part

1. Experimental Section

1.0 Isolation and Identification of Strains

*Klebsiella pneumoniae* 2302 as the host strain was isolated from Huashan Hospital affiliated to Fudan University, and stored in our laboratory. The other *Klebsiella pneumoniae* clinical strains were all from Huashan Hospital. According to the method of Brise (Wzi gene sequencing, a rapid method for determination of capsular type for *Klebsiella* strains. J. Clin. Microbiol. 51, 4073-4078.), the strain was sequenced and identified by the wzi method. These clinical isolates were cultured in LB medium at 37° C. and stored at −80° C. with glycerol.

1.1 Isolation of Bacteriophages

The bacteriophages were isolated from biological wastewater using Streptococcus pneumoniae isolate 2302. The untreated water sample was centrifuged, infected with *Klebsiella pneumoniae* strain 2302, and cultured in LB liquid medium with shaking at 37° C. overnight. The supernatant was filtered with a 0.22 μm filter (Millex-GP filter device; Micropore, USA); after a gradient dilution with SM buffer (100 mM NaCl, 8 mM $MgSO_4.7H_2O$, 50 mM Tris-HCl, pH=7.5) the solution was plated on LB medium containing 1.5% agar. After the upper layer had solidified, the plate was placed in a 37° C. incubator overnight. The next day, bacteriophage plaques were found on the double-layer agar plate covered with *Klebsiella pneumoniae* 2302. A single plaque was picked out for bacteriophage purification. The purified bacteriophage was obtained according to the method of Pires (Use of newly isolated phages for control of Pseudomonas aeruginosa PAO1 and ATCC 10145 biofilms. Res. Microbiol. 162, 798-806.). The bacteriophage titer was determined by the double-layer agar plate method. The lysed bacteriophage was obtained in the laboratory and was designated as SH-KP152302. The purified bacteriophage was amplified and then stored in SM buffer at 4° C.

1.2 Transmission Electron Microscopy

The bacteriophage was dropped onto a copper mesh with carbon film, after natural sedimentation, a drop of 2% phosphotungstic acid was added for staining.

After drying in the natural state, the bacteriophage was observed for its morphology using a transmission electron microscope.

1.3 Determination of Host Profile

Spotting assay and double-layer agar plate test were conducted on 27 clinical strains obtained in our laboratory for the host profile of SH-KP152302. In brief, 400 μL of bacterial culture was taken and mixed with 0.75% agar LB thoroughly, and then plated on 1.5% agar LB medium. After the top agar had solidified, 5 μL of the purified bacteriophage injectable suspension was dropped onto the lawn, then the effect of the bacteriophage on the bacteria was observed after incubating overnight at 37° C.

1.4 Extraction, Sequencing and Analysis of Bacteriophage Genomic DNA

10 μg/mL of deoxyribonuclease and ribonuclease A was added to the SM buffer containing bacteriophage, the mixture was treated at 37° C. for 1 h, and the bacteriophage was concentrated; the bacteriophage DNA was extracted to obtain 222,265 shear reads. The extracted bacteriophage DNA was sent to Shanghai Personal Biotechnology Co., Ltd. for genome sequencing, which was completed by the Illumina high-throughput sequencing platform (Illumina-Hiseq 3000). SOAP denovo2 software was used for gene assembly and optimization of results. The GeneMark software and Glimmer 3.02 software were used to predict and analyze the open reading frames (ORFs) of the bacteriophage genome. By using the BLAST online tool on the NCBI website, these genes to be predicted were compared with known sequences and annotated.

Through the analysis of bacteriophage genome DNA, we found an open reading frame sequence No. 43 (ORF43, also known as Dpo43), which contains 1926 bases and may be transcribed into a polypeptide chain or protein containing 641 amino acids. The HHpred software was used to analyze whether there is a protein structure similar to ORF43 encoded protein in the protein database.

1.5 Gene Cloning, Expression and Purification of Recombinant Depolymerase

The ORF43 gene fragment (1926 bases) encoding depolymerase was designed and amplified from the DNA of the purified bacteriophage SH-KP152302 using primer K47-orf43-F (5'-CAGCAGACGGGAGGATCCATGT-TAAACAACCTGAACCAGC -3') and K47-orf43 -R (5'-CTCGAGTGCGGCCGCAAGCTTTTATGGACCGATA ACCACAC-3'). Then, the amplified product was digested by BamH I and HindIII, and then cloned into the pSUMO3 expression vector with a N-terminal His tag. After the recombinant plasmid was verified by DNA sequencing, it was transformed into *E. coli* BL21 (DE3). BL21 (DE3)/pSUMO3-Dpo43 was inoculated into 1L of liquid LB medium containing 50 μg/mL ampicillin, and incubated to $OD_{600}$ of 0.4~0.8 at 37° C. and 220 rpm. Subsequently, 0.1 mM IPTG (isopropyl-β-D-thiogalactopyranoside) was added for inducing for 4h at 37° C., and the bacteria were harvested for protein expression and purification. The bacterial precipitation was resuspended in 20 mL lysis buffer (50 mM Tris-HCl, 500 mM NaCl, 10% glycerol, 20 mM imidazole, pH=7.5) containing PMSF, and lysed in an ice bath with ultrasound; the mixture was centrifuged at 4° C. with 12000 rpm for 1 h, and the supernatant was obtained and then subjected to protein purification using a nickel ion column. After equilibrating, the Ni column was washed with 20 mM and 40 mM lysis buffer, respectively, and finally eluted with elution buffer (20 mM Tris-HCl, 50 mM NaCl, 300 mM imidazole, pH=7.5) to obtain the fusion protein SUMO-dpo43. The obtained protein was subjected to SDS-PAGE electrophoresis and Coomassie brilliant blue staining, and enriched by centrifugation through a 30 KD filter membrane (Thermo, USA), finally the sample was stored at −80° C.

1.6 Purification of Exopolysaccharide (EPS)

The *Klebsiella pneumoniae* 2328 was inoculated into a fresh TSB medium and cultured overnight, stood and incubated in an incubator at 37° C. for 5 days, and then subjected to EPS purification. The specific steps are as follows:

60 μL of formaldehyde solution (36.5%) was added to 10 mL of bacterial culture, the mixture was incubated at 100 rpm for 1 h; 1 M NaOH was added, and the mixture was stirred for 3 h, and then centrifuged at 16,800 g for 1 h to separate polysaccharides (supernatant) and bacteria precipitation; trichloroacetic acid (TCA, 20% w/v) was added to the supernatant for precipitating to remove protein and nucleic acid. The solution was centrifuged at 16,800 g for 1 h, and a supernatant was collected; 1.5 times of the volume of 96% ethanol was added, and exopolysaccharide (EPS) was precipitated after standing at −20° C. for 24 h; then the solution was centrifuged at 16800 g for 1 h, and the precipitation was resuspended in double distilled water (ddH$_2$O); the EPS mixture was dialysed in ddH$_2$O at 4° C. overnight using a 12~14 kDa dialysis bag to remove small molecular impurities, and finally the obtained EPS after dialysis was lyophilized and weighed.

1.7 Determination of the Activity of Depolymerase Dpo43

1.71 Spotting Method

The spotting method was used to identify the degradation effect of the recombinant enzyme on *Klebsiella pneumoniae*: the exponentially growing bacteria were inoculated on LB soft agar, and after drying, 10 µL enzyme solution was added and incubated overnight at 37° C. The formation of a halo indicated that the strain was sensitive to the depolymerase, and the enzyme solution was gradient diluted, and then the activity range was determined. The SUMO protein was the negative control group. In addition, the functional microflora of the recombinant protein was determined by the spotting method. The purified recombinant protein Dpo43 and the published Dpo42 protein were added dropwise to all the host strains of SH-KP152302 bacteriophage at the same time, and the degradation effects of the two proteins on K47 *Klebsiella pneumoniae* were observed.

1.72 High Performance Liquid Chromatography (Size Exclusion High-Performance Liquid Chromatography, SEC-HPLC) Detection In order to prove that the recombinant Dpo43 protein has a depolymerase activity on *Klebsiella pneumoniae* polysaccharides, we used high-performance liquid size exclusion chromatography (HPLC-SEC) to analyze the depolymerization experiments. In the experiment, the purified EPS (final concentration of 0.5 mg/ml) and Dpo43 (10 µg/ml) were added to 50 mM Na$_2$HPO$_4$ (pH 7.0) and incubated at 37° C. for 30 min. After the incubation, the reaction was ended by heating at 100° C. for 15 min.

Perform HPLC analysis: the sample has a volume of 20 µL, solution A (0.2 M phosphate buffer) was used as the mobile phase for 30 min, and the chromatographic analysis was performed at a flow rate of 0.5 mL/min. The depolymerase activity may be analyzed by comparing the peak profiles before and after degradation.

1.8 Analysis of Enzyme Activity and Stability of Depolymerase

The activity and stability of Dpo43 enzyme were analyzed at different pH and temperature. Based on that the exopolysaccharides may be degraded into reducing sugars under the effect of polysaccharide depolymerase, the amount of reducing sugars produced was determined by Miller method (determination of reducing sugar with dinitrosalicylic acid reagent), thus the activity level of polysaccharide depolymerase was presumed and determined. Glucose was used as a standard, with a concentration gradient of 0.2-1.0 mg/mL.

A solution of 500 L was added to each tube, followed by 1.5 mL DNS reagent, then the mixture was thoroughly mixed and incubated at 37° C. for 30 min. After the completion of the reaction, the reaction was terminated by boiling in a water bath kettle at 100° C. for 10 min. The mixture was quickly cooled to room temperature, and ddH$_2$O was added in a ratio of 1:5 (vol/vol), then the absorbance value was measured at 550 nm and a standard curve was plotted. The enzyme activity was detected by calculating the amount of monosaccharide released by the action of the enzyme through the standard curve. First, the activity of depolymerase Dpo43 was measured under different pH conditions, and different pH buffer systems were set as follows: 50 mM sodium acetate (pH 2.0~5.0), 50 mM Na$_2$HPO$_4$ (pH 6.0~7.0), 50 mM Tris-Hcl (pH 8.0~9.0), and 100 mM NaHCO$_3$ (pH 10.0~11.0), and the optimal reaction pH was obtained. Similarly, when determining the activity of the depolymerase Dpo43 at different temperatures, the depolymerase Dpo43 was acted at 25° C., 37° C., 50° C., 70° C., 80° C., and 90° C., and 50 mM Na$_2$HPO$_4$ (pH 6.0) was used as the buffer. The enzyme activity under different conditions is expressed by the relative enzyme activity compared with that under the optimal conditions. In order to determine the stability of the enzyme activity under different conditions, Dpo43 was pre-incubated for 30 min under different temperature and pH conditions, and then the enzyme activity was measured according to the above method.

2. Results

2.1 Clinical Isolation of the Capsule *Klebsiella Pneumoniae*

All the 27 clinical strains were carbapenem drug-resistant *Klebsiella pneumoniae*. Wzi sequencing method was used to determine the typing of clinically isolated strains. All strains were type K47, wherein *Klebsiella pneumoniae* 2302 was used as the host strain of bacteriophage.

2.2 Isolation of Bacteriophages

Specific bacteriophage (named SH-KP152302) was isolated from hospital sewage using carbapenem drug-resistant *Klebsiella pneumoniae* Kp2302 as an indicator bacteria. The bacteriophage suspension was plated onto the semi-solid plate with Kp2302 bacteria using the two-layer agar plate method, which could form transparent bacteriophage plaques, and a faint halo could be seen around the bacteriophage plaque (FIG. 1).

2.3 Microbial Characteristics and Lysis Profile of SH-KP152302

Figure 2:
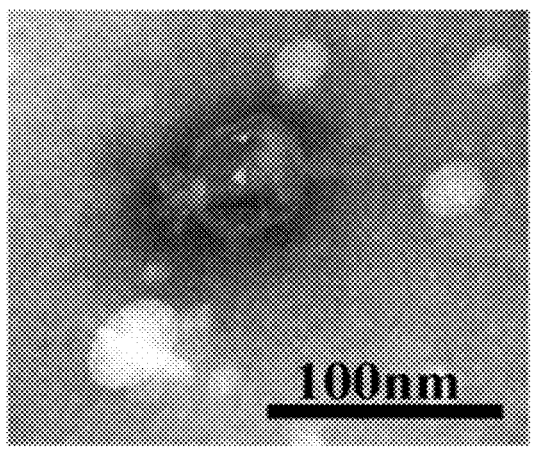
FIG. 2 is an electron microscopy image of bacteriophage SH-KP152302 according to an embodiment of the present disclosure.

Observed by transmission electron microscope, we found that the head of the bacteriophage is a hexagon in different sizes, with a diameter of 50 nm and a tail of 20 nm×10 nm. Based on these morphological characteristics, the bacteriophage was presumed to be a member of the podoviridae family (FIG. 2). Previous studies have been shown that the appearance of translucent aureoles means the presence of polysaccharide depolymerase, which is a capsular polysaccharide degrading enzyme of bacteriophage. Therefore, we speculated that the capsule type of bacterial may be involved in the bacteriophage infection. To prove this hypothesis, we evaluated the conditions of 27 K47 capsular clinical strains infected by the bacteriophage SH-KP152302 based on the spotting assay and the double-layer agar plate test. It was found from the results that other K47 *Klebsiella pneumoniae* can also be lysed by this bacteriophage except for the host strain (2302) (Table 1). The results showed that the bacteriophage SH-KP152302 is highly sensitive to the K47 host strain.

TABLE 1

Strain information and bacteriophage lysis profile

| Strains | K typing | SH-KP152302 |
| --- | --- | --- |
| K14 | K47 | + |
| k19 | K47 | + |
| k20 | K47 | + |
| Blood 18 | K47 | + |
| Blood 20 | K47 | + |
| Blood 32 | K47 | + |
| Blood 34 | K47 | + |
| Hybrid 103 | K47 | + |
| Hybrid 105 | K47 | + |
| Hybrid 114 | K47 | + |
| Hybrid 117 | K47 | + |
| Hybrid 119 | K47 | + |
| Hybrid 13 | K47 | + |
| Hybrid 14 | K47 | + |
| Hybrid 23 | K47 | + |
| Hybrid 42 | K47 | + |
| Hybrid 47 | K47 | + |
| Hybrid 51 | K47 | + |
| Hybrid 56 | K47 | + |
| Hybrid 70 | K47 | + |
| Hybrid 72 | K47 | + |
| Hybrid 77 | K47 | + |
| Hybrid 80 | K47 | + |
| Hybrid 92 | K47 | + |
| 2226 | K47 | + |
| 2302 | K47 | + |
| 2328 | K47 | + |

2.4 Genome Analysis of Bacteriophage SH-KP152302

Figure 3:
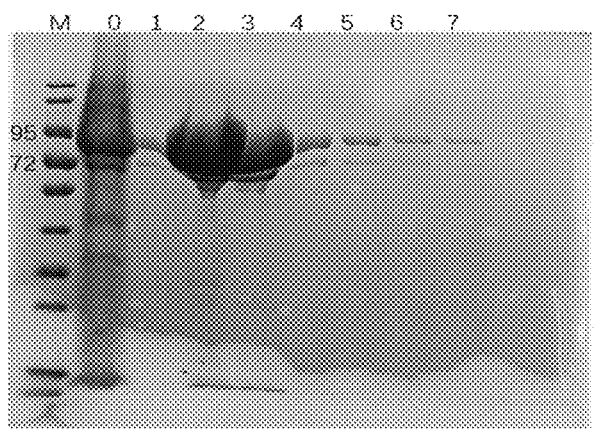
FIG. 3 is an SDS-PAGE electrophoretogram of recombinant SUMO-Dpo43 fusion protein purified by Ni column according to an embodiment of the present disclosure; M: protein marker; lanes 1-6: collected target protein.

The whole genome sequencing showed that the nucleotide sequence of SH-KP152302 is a double-stranded linear genome containing 41420 base pairs (bp), with a GC content of 52.70%, containing 48 open reading frames (ORFs), and an average length of 766 bp. The annotation of the genome sequence indicated that functional proteins have 28 distinct functional genes, which may be divided into 4 types: DNA assembly and morphology-related proteins, DNA replication/recombination/modification proteins, host lysing proteins, and unclassified proteins. The rest are putative functional proteins without toxicity and drug-resistant genes. (FIG. 3)

According to genomic analysis, ORF43 is a predicted tail fiber protein and may be a candidate depolymerase gene. The sequence alignment (BlastP) result of ORF43 gene showed that, no known conserved structure or functional domain was found in this sequence. However, a moderately homologous protein was found in the protein database (PDB) using HHpred's sequence identity analysis. The HHpred results showed that the protein encoded by this gene has a high structural similarity with the tail tip protein contained in the bacteriophage phi297 of Pseudomonas, and the tail tip protein of phi297 has an enzyme activity domain of pectin lyase. In summary, all informations indicated that the product of ORF43 gene may be the capsular depolymerase in bacteriophage SH-KP152302.

The DNA sequence of Dpo43 is represented by SEQ ID NO: 4.

Dpo43 has a protein sequence of:

```
                                      (SEQ ID NO: 2)
MLNNLNQPKGSTIGVLKDGRTIQQAIDGLENPVHYVKDVSITPSALLA

VAVEAARLGRTVEFGPGHYTNQGQPFEVDFPLNLDVPVGTFLDFPIII

RGKTVKMVRSVATNLTAAQCPAGTTVIAGDFSAFPVGSVVGVKLGDNT

NGSASYNNEAGWDFTTVAAASNTSITLSTGLRWAFDKPEVFTPEYAVR

YSGQLSRSSYFIPGDYTSGLNVGDIIRVENIDGTDGVHGNKEYFEMLK

VSSIDSSGITVETRLRYTHVNPWIVKTGLVKGSSVTGGGRLKRLEVRG

VDTPKVNNVDVDRLIVGLCYNIDVGEITSRGVGEPSSVNFTFCFGRGF

LYNVRASGSVSTTDNSALKLMSCPGLIINNCSPHNSTSTGSQGDYFGY

VDAYYPPYWCWNDGMSINGIVTETPRSAVTRALWLFGLRGCSVSNLSG

AQVFLQGCAKSVFSNIVTPDNLLELRDLSGCIVSGMANNALVLGCWNS

TFDLTLFGIGSGSNLNIALRAGAGVTHPETGVPTTLGKNNTFNVKSFS

PSSLAVTLSIAQQERPIFGAGCVDVDSANKSVTLGSNVTVPTMLPLAL

TKGIDSGSGWVGGRTKGGIWFDGNYRDAAVRWNGQYVWVADNGSLKAA

PTKPDSDSPSNGVVIGP.
```

2.5 Cloning and Expressing of Bacteriophage Depolymerase Dpo43

The recombinant plasmid pSUMO3-Dpo43 was transferred into BL21 (DE3), after culturing on the ampicillin resistant plate overnight, monoclonal colonies were picked out and cultured in 50 mL liquid medium until $OD_{600}$ reaches 0.4~0.8. IPTG was added with a final concentration of 0.1 mm, and the expression was induced at 37° C. for 4 h. After ultrasonic crushing, centrifugation was performed. The supernatant was taken, and then subjected to protein purification using nickel ion column. The purified protein was heated and denaturated, and then subjected to SDS-PAGE protein electrophoresis. FIG. 3 shows that the purified recombinant SUMO-Dpo43 fusion protein migrates in a single band form on SDS-PAGE, and a protein band was found at around 87 kDa. This protein is consistent in terms of the molecular weight with the expected fusion protein, and is the correct expression product of the positive recombinator.

2.6 Verification for the Activity of Recombinant Depolymerase

Figure 4:
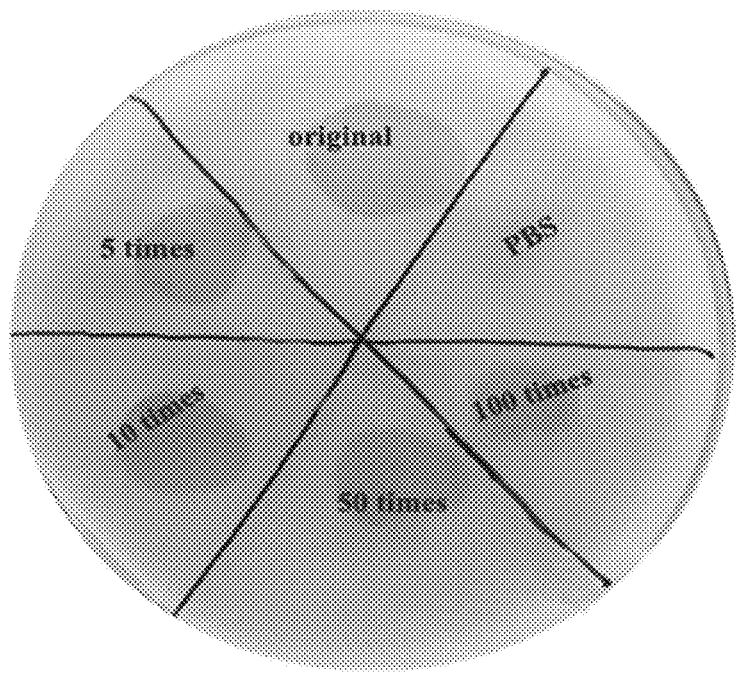
FIG. 4 is a spotting assay of gradient dilution of Dpo43 in the host strain Kp2328 according to an embodiment of the present disclosure; PBS is used as the control.
Figure 5:
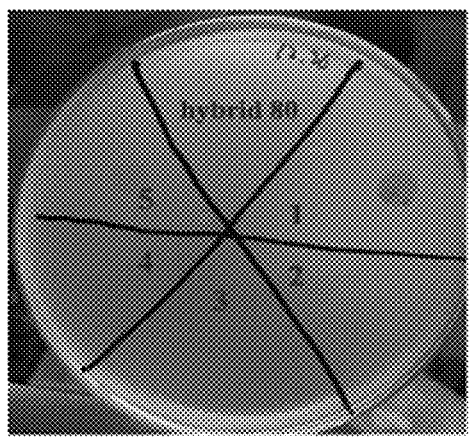
FIG. 5 is a spotting assay of depolymerases Dpo42 and Dpo43 on different K47 *Klebsiella pneumoniae* hybrid 80 and hybrid 92 respectively according to an embodiment of the present disclosure, bacteriophage is used as the positive control, and SUMO protein and PBS are used as negative controls.
Figure 5:
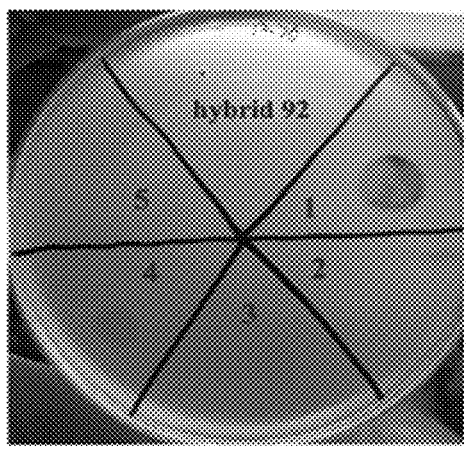

In order to verify whether ORF43 gene product has an activity of polysaccharide depolymerase, the purified recombinant protein was diluted at different concentrations (0.5 μg/mL 5 mg/ml), then dropped onto the two-layer agar plate plated with Kp2328 for overnight incubation. The generation of transparent halo could be observed (FIG. 4). In addition, the spotting assay of the host of depolymerase showed that, the recombinant protein Dpo43 and the published Dpo42 have complementary lysis effects on 27 K47 *Klebsiella pneumoniae* (Table 2), for example, against different K47 pneumonia *klebsiella* bacteria hybrids 80 and 92, bacteriophage has a lysis effect on both strains, but the two lyases show different effects (in Table 2, + means lysis effect, − means no lysis effect). The results indicated that Dpo43 and Dpo42 may play different depolymerase roles for different K47 *Klebsiella pneumoniaes*, and the hydrolysis sites may be different (FIG. 5).

TABLE 2

Strain information and lysis profiles of depolymerases Dpo42 and Dpo43

| Strains | K typing | Dpo42 | Dpo43 |
|---|---|---|---|
| K14 | K47 | − | + |
| K19 | K47 | − | + |
| K20 | K47 | + | − |
| Blood 18 | K47 | − | + |
| Blood 20 | K47 | + | − |
| Blood 32 | K47 | − | − |
| Blood 34 | K47 | + | − |
| Hybrid 103 | K47 | − | + |
| Hybrid 105 | K47 | − | + |
| Hybrid 114 | K47 | − | + |
| Hybrid 117 | K47 | − | + |
| Hybrid 119 | K47 | − | + |
| Hybrid 13 | K47 | − | + |
| Hybrid 14 | K47 | + | − |
| Hybrid 23 | K47 | + | − |
| Hybrid 42 | K47 | + | − |
| Hybrid 47 | K47 | + | − |
| Hybrid 51 | K47 | − | + |
| Hybrid 56 | K47 | − | − |
| Hybrid 70 | K47 | − | + |
| Hybrid 72 | K47 | − | + |
| Hybrid 77 | K47 | + | − |
| Hybrid 80 | K47 | − | + |
| Hybrid 92 | K47 | + | − |
| 2226 | K47 | + | − |
| 2302 | K47 | + | − |
| 2328 | K47 | − | + |

Figure 6:
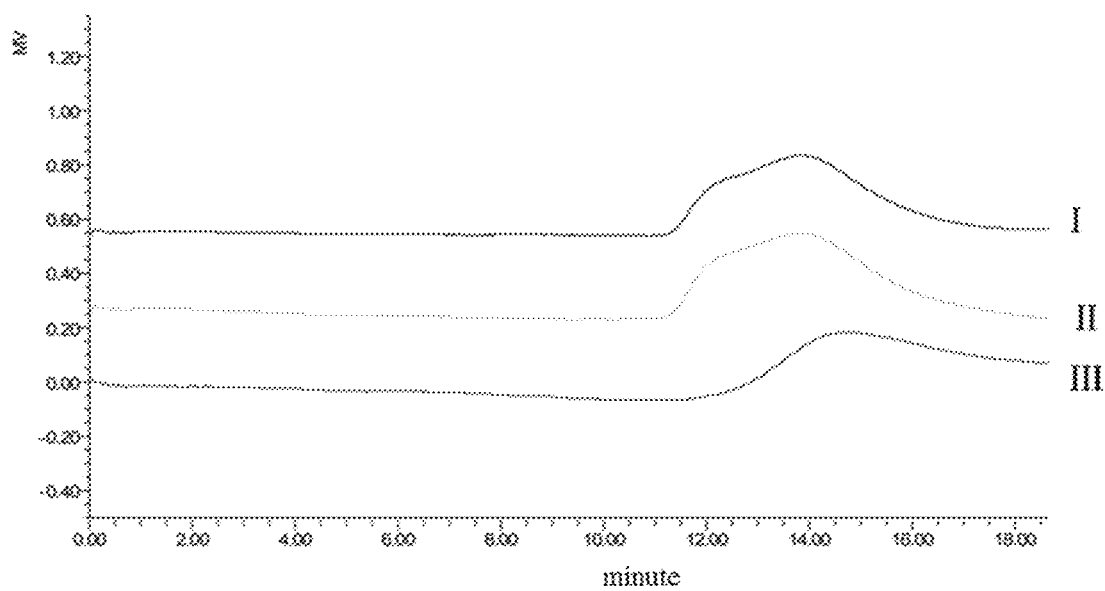
FIG. 6 shows the results of HPLC detection for Dpo43 according to an embodiment of the present disclosure, wherein I-untreated EPS solution, II-EPS and SUMO were incubated at 37° C. for 30 minutes, and III-EPS and Dpo43 were incubated at 37° C. for 30 minutes.

Subsequently, we extracted and purified EPS from *Klebsiella pneumoniae* strain 2328 to verify its enzyme activity. As shown in FIG. 6, in the high performance liquid molecular sieve chromatography, the unprocessed EPS sample showed a peak within 11-16 min. After SUMO treatment, the peak still exists and the peak patterns are the same; while after culturing with Dpo43 (10 μg/ml) for 30 min at 37° C., the rentention time of polysaccharides of high molecular weight rearward shifted and the peak pattern became smaller, indicating that EPS was degraded by Dpo43 enzyme. In the control group, SUMO has no degradability. These results indicated that the EPS of *Klebsiella pneumoniae* 2328 may be degraded by Dpo43.

2.7 Characterization of Depolymerase Activity

Figure 7:
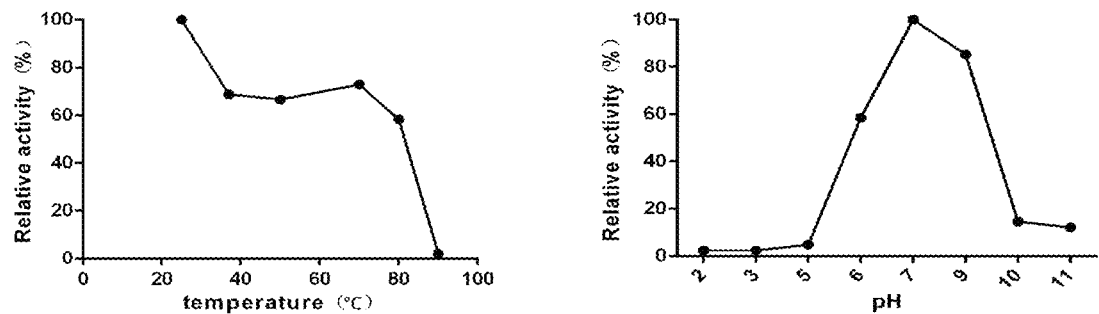
FIG. 7 shows the effects of temperature and pH on the activity of Dpo43 according to an embodiment of the present disclosure; A shows the effect of different temperatures on the activity of depolymerase Dpo43; B shows the effect of different pH on the activity of depolymerase Dpo43; C shows the activity of depolymerase after standing at different pH for 30 min; D shows the activity of depolymerase after standing at different pH for 30 min.
Figure 7:
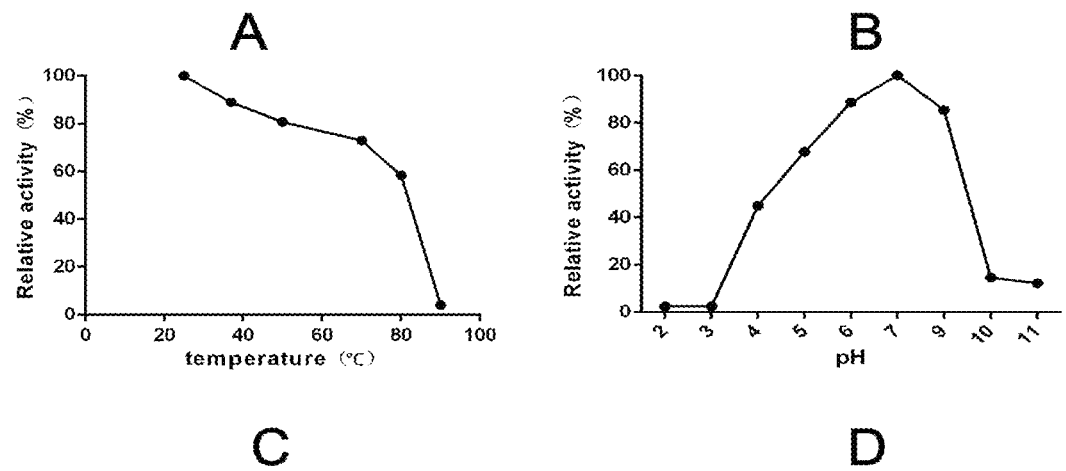

Polysaccharide depolymerase can degrade capsular polysaccharides into reducing sugars. The optimal enzyme activity of polysaccharide depolymerase Dpo43 at different pH and temperatures was further studied by determining the amount of reducing sugars produced with DNS method. As shown in A of FIG. 7, the optimal reaction temperature of depolymerase Dpo43 was 25° C., while it has good enzyme activity between 30° C. and 70° C., indicating that the enzyme has a good thermal stability, but the enzyme completely lost the enzyme activity at 90° C. B in FIG. 7 showed that the depolymerase Dpo43 had an activity at pH=5-10, and the enzyme activity was highest around pH=7. The remaining activity of the depolymerase Dpo43 after being standing at different temperatures for 30 min is shown in C of FIG. 7. When the temperature is 25-70° C., the enzyme may retain most of the enzyme activity; when the temperature is higher than 70° C., the activity of the enzyme was significantly reduced, indicating stability at a wider range of temperature. D in FIG. 7 showed that the enzyme still has a high activity at a pH of 4.0-9.0, indicating stability at a wide range of pH.

Figure 8:
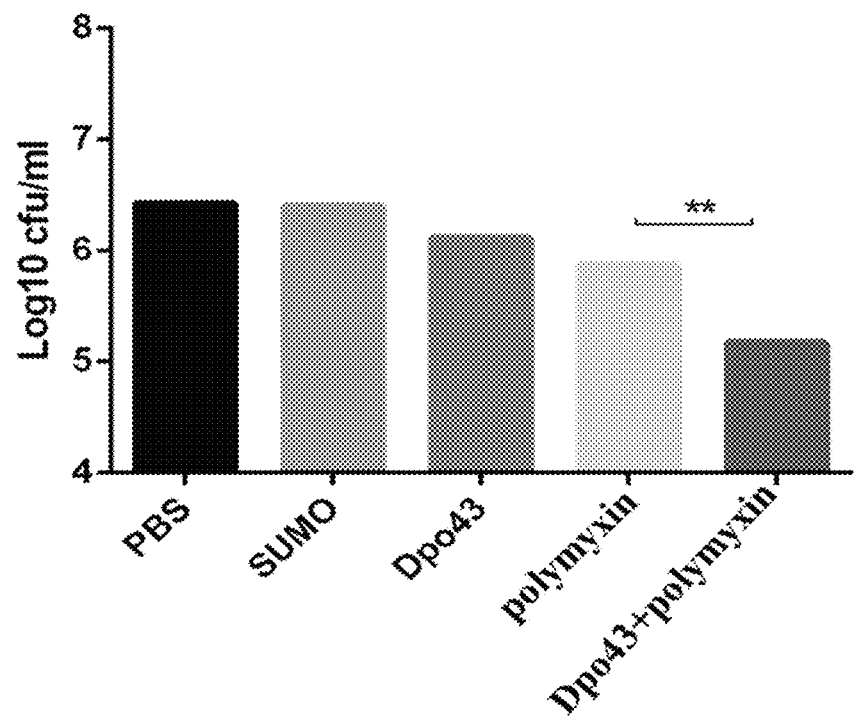
FIG. 8 shows the effect of depolymerase Dpo43 in combination with polymyxin on the *Klebsiella pneumoniae* biofilm according to an embodiment of the present disclosure.

2.8 The Effect of Depolymerase Dpo43 Combined with Polymyxin on *Klebsiella pneumoniae* Biofilm A combination of depolymerase Dpo43 and polymyxin was used to investigate whether the depolymerase Dpo43 and polymyxin have a synergistic anti-biofilm effect. The results showed that compared with the control group, the average number of bacteria in the two groups added with Dpo43 or polymyxin decreased to a certain extent (FIG. 8), while the average number of bacteria in the group of depolymerase Dpo43+ used in combination with polymyxin decreased significantly, and the decrease is more obvious compared with the two groups added separately. These results indicated that the depolymerase Dpo43 enhances the bactericidal activity of polymyxin by degrading *Klebsiella pneumoniae* biofilm.

EXAMPLE 2 Dpo42 PART

Example 2.1 Isolation and Purification of Bacteriophages

Sewage samples were taken from Huashan Hospital affiliated to Fudan University. The water samples were centrifuged and then *Klebsiella pneumoniae* was added, the mixture was cultured overnight at 37° C. with shaking. Pacteriophages and bacteria were concentrated in the supernatant; the supernatant was filtered through 0.22 μm filter membrane, and gradient diluted into SM buffer (100 mM NaCl, 8 mM $MgSO_4.7H_2O$, 50 mM Tris-HCl, pH=7.5), and then spotted onto a double-layer agar plate for bacteriophage isolation;

The bacteriophage plaques were purified until single plaque morphology appeared on the plate; 3 mL SM buffer solution was added into the plate, the mixture was stirred at 120 rpm, and stood overnight at 4° C.; the liquid and the top layer agar were collected and centrifuged at 9,000×g for 15 min. The supernatant was filtered through a 0.22 m filter membrane, and the purified bacteriophages were stored in the SM buffer at 4° C.; the bacteriophage particles were enriched with PEG-8000 overnight, then subjected to cesium chloride density gradient centrifugation at 20000×g for 1 hour to obtain purified bacteriophage.

Figure 9:
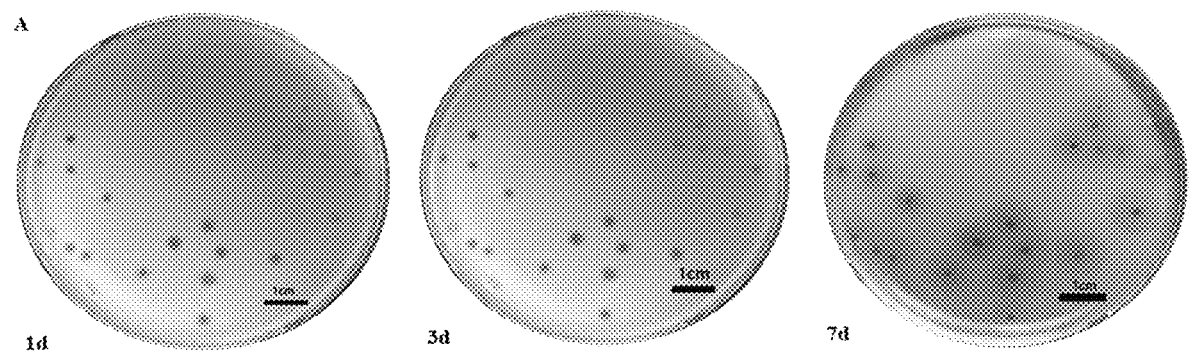
FIG. 9(A) is a bacteriophage plaque according to an embodiment of the present disclosure.
FIG. 9(B) is a transmission electron micrograph of the morphology of the bacteriophage according to an embodiment of the present disclosure.
Figure 9:
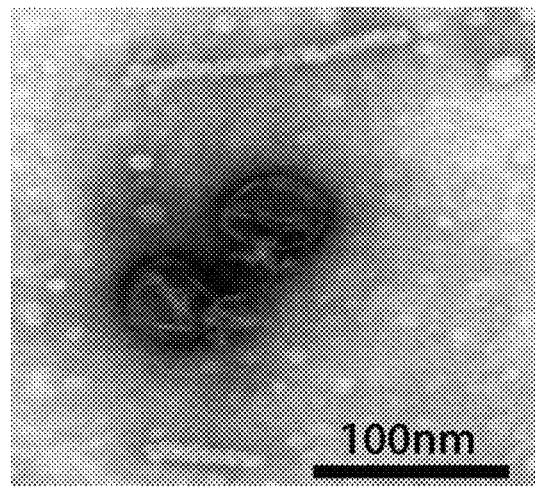

As shown in FIG. 9(A), after a long period of culture, an increasing halo around the bacteriophage plaque was produced. After 12 h, the pure bacteriophage plaque appeared, and 3-7 days later, the aureole around the plaque increased, indicating that the bacteriophage had an activity of polysaccharide depolymerase; As shown by the transmission electron microscope in FIG. 9(B), the morphology of the podoviridae is 50 nm of the head and 20 nm×10 nm of the tail.

Example 2.2 Determination of the Principal Spectrum

In this example, the lysis profile of 97 carbapenem drug-resistant *Klebsiella pneumoniae* bacteriophages were detected. Bacteria grew overnight at 37° C. 200 μL bacterial culture was taken and inoculated on a double-layer agar plate. After top agar has been solidified, 10 μL of gradient diluted bacteriophage was added; after overnight incubation at 37° C., the effect of bacteriophage on bacteria was observed and scored.

The results found that in addition to the host strain (2302), the bacteriophages of other *Klebsiella pneumoniae* (0523, 0581, 0775, 0805, 0861, 1093, 1109, 2226, 2302, 2328, 2340) all formed obvious plaques with surrounding aureoles. According to the results of wzi sequencing, all the strains belong to the K47 capsule typing.

Example 2.3 Isolation, Sequencing and Annotation of Bacteriophage Genomic DNA

10 μg/mL of deoxyribonuclease and ribonuclease A was added to the SM buffer containing bacteriophage, the mixture was treated at 37° C. for 1 h, and the bacteriophage was concentrated; the bacteriophage DNA was extracted to obtain 222,265 shear reads;

Glimmer 3.02 was used to analyze the open reading frames (ORFs) of the bacteriophage genome, Genemark was used to determine the predicted genes, BLAST was used to compare the predicted genes with known genes and protein sequences, and the HHpred database was used as a supplement to the annotation of polysaccharide depolymerase; in addition, considering the safety and stability of the bacteriophage in clinical application, ProParam software was used to analyze the stability of ORF-encoded protein, and the VFDB database was used to analyze CPG islands.

The results found that the nucleotide sequence of SH-KP152302 is a linear genome containing 41420 bp, with a GC content of 52.70%, containing 48 putative functional genes with an average length of 766 bp.

The functional proteins have 28 distinct functional genes, which may be divided into 4 types: DNA assembly and morphology-related proteins, DNA replication/recombination/modification proteins, host lysing proteins, and unclassified proteins. The rest are putative functional proteins without toxicity and drug-resistant genes.

The ORF42 encoded protein of bacteriophage SH-KP152302 is composed of 793 amino acids; the results of Blastp and HHpred showed that the ORF42 encoded protein was similar to the protein 5JS4 encoded by ORF49 of bacteriophage phiAB6 (GenBank ID: KT339321), but relatively low homology (14%).

ORF42 includes four conserved domains, namely T7 bacteriophage tail-fiber protein, pectate lyase, nitrogen-containing oxidase and β-helix domain; among them, the n-terminal domain encodes a tail-tube surrounded by 6 tail-fibers, which is a kind oligomer of viral protein gp17, belongs to the T7 bacteriophage tail-fiber protein, and may interact with the head structure of bacteriophage; the domain in the middle position encodes pectate lyase, which is a primary domain that destroys glycosidic bonds and lyses bacterial exopolysaccharides, and belongs to glycoside hydrolase family 28; the site adjacent to the pectate lyase domain encodes nitrogen-containing oxidase, which participates in the transport and metabolism of inorganic salt ions.

Example 2.4 Cloning, Expression and Purification of Bacteriophage Depolymerase

In this example, depolymerase encoding ORF42 was amplified from the genome of bacteriophage SH-KP152302 using specific primers (cgagctcatggaccaagacattaaaacagtc; and cccaagcttttactgttccccactgc), and SacI and HindIII (New England Biolab) restriction sites were introduced into both ends of the amplified product; the PCR amplified product, after digested with SacI and HindIII, was cloned into the pSUM03 expression vector, then the obtained orf42-pSUMO3 plasmid was transformed into *E. coli* BL21(DE3), BL21 (DE3)/pSUMO3-Dpo43 cell, well shook and incubated at 37° C. in 1 L of LB with 50 μg/mL ampicillin added, to $OD_{600}$ of 0.6.

The depolymerase was induced for recombinant expression by 0.5 mM IPTG (isopropyl-β-D-thiogalactopyranoside), incubated at 30° C. for 4 h, centrifuged (5000×g, 30 min, 4° C.) and granulated. Cells were thawed in 20 mL lysis buffer (50 mM Tris-HCl, 500 mM NaCl, 10% glycerol, 20 mM imidazole, pH=7.5) containing PMSF, and lysed on ice with ultrasound; the cell fragments were centrifuged at 4° C. and at 12000 rpm for 1 h, and then subjected to protein purification using a nickel ion column. After equilibrating with the lysis buffer, the supernatant was taken and washed with 20 mM lysis buffer, and eluted with elution buffer (20 mM Tris-HCl, 50 mM NaCl, 300 mM imidazole, pH=7.5) to obtain the fusion protein SUMO-dpo42.

The SUMO protease was added into the fusion protein SUMO-dpo42 at a ratio of protease to fusion protein of 1:5000 (wt/wt), and the mixture was dialyzed overnight in dialysis buffer (50 mM tris-Hcl, 50 mM NaCl, 10% glycerol, 20 mM imidazole, pH=7.5) at 4° C. The lytic protein solution was then reloaded onto the Ni-NTA column for the removal of histidine labeled SUMO and the undigested fusion protein; the obtained protein was subjected to SDS-PAGE electrophoresis and Coomassie brilliant blue staining, and enriched by centrifugation through a 30 KD filter membrane (Thermo, USA), finally the sample was stored at −80° C.

Figure 10:
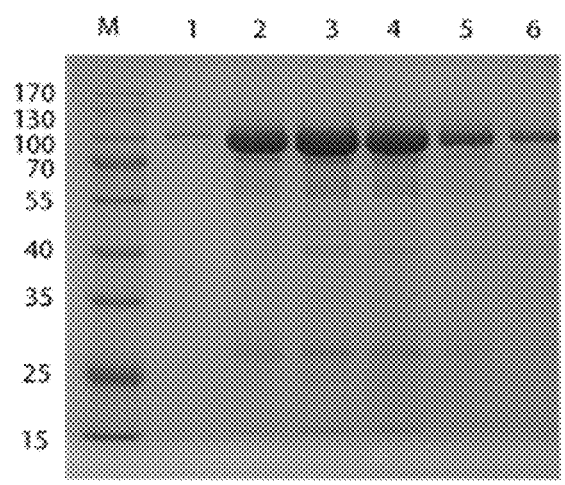
FIG. 10(A) is an SDS-PAGE electrophoretogram of the SUMO-Dpo42 fusion protein according to an embodiment of the present disclosure, wherein, M: protein marker, 1-6: fusion protein.
FIG. 10(B) is an SDS-PAGE electrophoretogram of the eluted protein according to an embodiment of the present disclosure, wherein, M: protein marker, 1: fusion protein, 2: digested protein, 3: nickel column-attached protein, 4: purified protein, 5: eluent.
Figure 10:
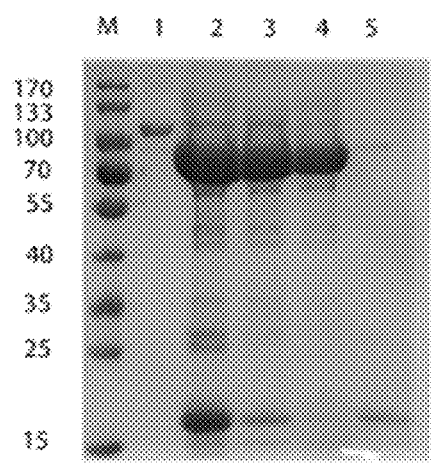

As shown in FIG. 10(A), the purified recombinant SUMO-Dpo42 fusion protein migrated in a single band form on SDS-PAGE, corresponding to the protein marker of about 102 kDa; after the SUMO label of SUMO-dpo4 fusion protein has been lysed efficiently using SUMO protease, SDS-PAGE electrophoresis was carried out, as shown in FIG. 10(B), the 6×His labeled SUMO and undigested fusion proteins were removed, and the purified depolymerase was about 85 kDa.

After sequencing and identification, it is known that the nucleotide sequence of Dpo42 is represented by SEQ ID NO: 3;

Dpo42 has an amino acid sequence of:

```
                                          (SEQ ID NO: 1)
MDQDIKTVIQYPVGATEFDIPFDYLSRKFVRVSLVSDDNRRLLSNITE

YRYVSKTRVKLLVETTGFDRVEIRRFTSASERIVDFSDGSVLRASDLN

VSQIQSAHIAEEARDAALMAMPQDDAGNLDARNRRIVRLAPGIAGTDA

VNKDQLDTTLGEAGGILSDMKDLEGEIHDYIEKFADDTALVRGVAWVY

NLGSADGGETVITINKSTRTYAVPYIEVNGSRQEVGYHYSFDLETQQI

TLATPLKAGDFVMVMTTESQLPVETLLASSVGAASIGTATGETVEERL

TRLYGHFVHPETYGAVGDGITDDRVALQRSLDVAYENALNGTGPSTVR

WSGDYMVSLNPNSLGVSGELAAGRSALCIRPGVSIEGKGTVRLDPSFT

GSQSGAVITNWAGPADDCSIKDIRIYGGKDVATGTGITGILILDSQRV

VISDVKVLNSTAGGIYLRKGATEGLYGCSFSKVSGCTVDNAGYIGIQM

ERPYDNTVIGNTINRCEDNGIDVFGNVNDATVTGIAQSTLITGNNIRD

VLNGVFIESCGNTNITGNYIADFRSSGVIYNRINSAANDNSLTSNVLI
```

-continued

```
GASGASAGVSFKNSVGYCTVASNRIQNSDYGIRCVGGGITGLNILPNT

MKNIAKTLLFVEARNNGLVKSRMSTQFYEGAQVGGIPSNTSPRGVPHR

FPSRLSYIVDIQPFWATEQGTREDNFERAKGTLASITGWGSKCALYDT

IVAGDTVVSLNSSSVAVGEYLEINAEVYKVTSVSATYAVVRKWTGSDY

TAGDYAAVIISNPSYIIRRVQWGEQ.
```

Example 2.5 Purification of Bacterial EPS

The *Klebsiella pneumoniae* 2226 was inoculated into a fresh TSB medium and cultured overnight, and incubated at 37° C. for 5 days without stirring, and then subjected to EPS purification. The specific steps are as follows:

60 μL of formaldehyde solution (36.5%) was added to 10 mL of bacterial culture, the mixture was incubated for 1 h with gently shaking (100 rpm); 1 M NaOH was added, and the mixture was stirred for 3 h, then EPS was extracted; the cell suspension was centrifuged at 16800×g for 1 h, trichloroacetic acid (TCA, 20% w/v) was added to precipitate the supernatant for removing protein and nucleic acid. The solution was centrifuged at 16800×g for 1 h, then a supernatant was collected; 96% ethanol was added at 1.5 times of the volume, and exopolysaccharide (EPS) was precipitated after stored at −20° C. for 24 h; the obtained precipitation was centrifuged at 16,800×g for 1 h, and resuspend in double distilled water (ddH$_2$O); the EPS mixture was dialysed in excessive ddH$_2$O at 4° C. for 24 h, and the low-molecular weight impurities were removed using a filter membrane of 12~14 kDa molecular weight, finally the obtained EPS after dialysis was lyophilized and weighed.

Example 2.6 Formation of Biofilm

*Klebsiella pneumoniae* was cultured overnight at 37° C., then diluted by adding fresh TSB medium and cultured until OD$_{600}$=0.1, a biofilm was formed after 48 h and 72 h, 200 μL fresh TSB medium was used as a negative control; after incubation, the supernatant was taken and rinsed twice with 200 μL 1×PBS buffer, then each well was treated with 200 μL methanol (10% v/v) at room temperature for 15 min; the methanol was removed, and each well was dried at room temperature, then 200 μL crystal violet (1% v/v) was added for incubating for 20 min, and then rinsed with sterile water gently; the stained solution was dissolved by adding 100 μL acetic acid (33% v/v); the absorbance was measured at 595 nm and the experiment was repeated three times.

Example 2.7 Functional Analysis of Depolymerase

The spotting method was used to identify the degradation effect of the recombinant enzyme on *Klebsiella pneumoniae*: the exponentially growing bacteria were inoculated on LB soft agar, and after drying, 10 μL enzyme solution was added and incubated overnight at 37° C. The formation of a halo band indicated that the strain was sensitive to the polymerase, and the enzyme solution was gradient diluted, and then the activity range was determined. The SUMO protein was the negative control group.

Figure 11:
FIG. 11 is a spotting experiment of gradient dilution of Dpo42 on the host bacteria according to an embodiment of the present disclosure, and SUMO is used as the control.

As shown in FIG. 11, the gradient dilution of polymerase solution formed a halo ring on the bacterial culture plate.

In order to identify Dpo42 as a polysaccharide depolymerase, high-performance liquid size exclusion chromatography (HPLC-SEC) was used to evaluate the degradation activity of Dpo42. The specific steps are as follows:

The purified EPS was dissolved in 50 mM Na$_2$HPO$_4$ (pH=7.0) and incubated at a final concentration of 0.5 mg/mL with Dpo42 (0.1 μM) or SUMO (0.1 μM) at 37° C. for 30 min; heated at 90° C. for 10 min, then the reaction was stopped and subjected to HPLC analysis; the sample volume was 20 μL, solution A (0.2 M phosphate buffer) without solution B was used as the elution system; solution A was used as the mobile phase within 30 min, and the chromatographic analysis was performed at a flow rate of 0.5 mL/min.

Figure 12:
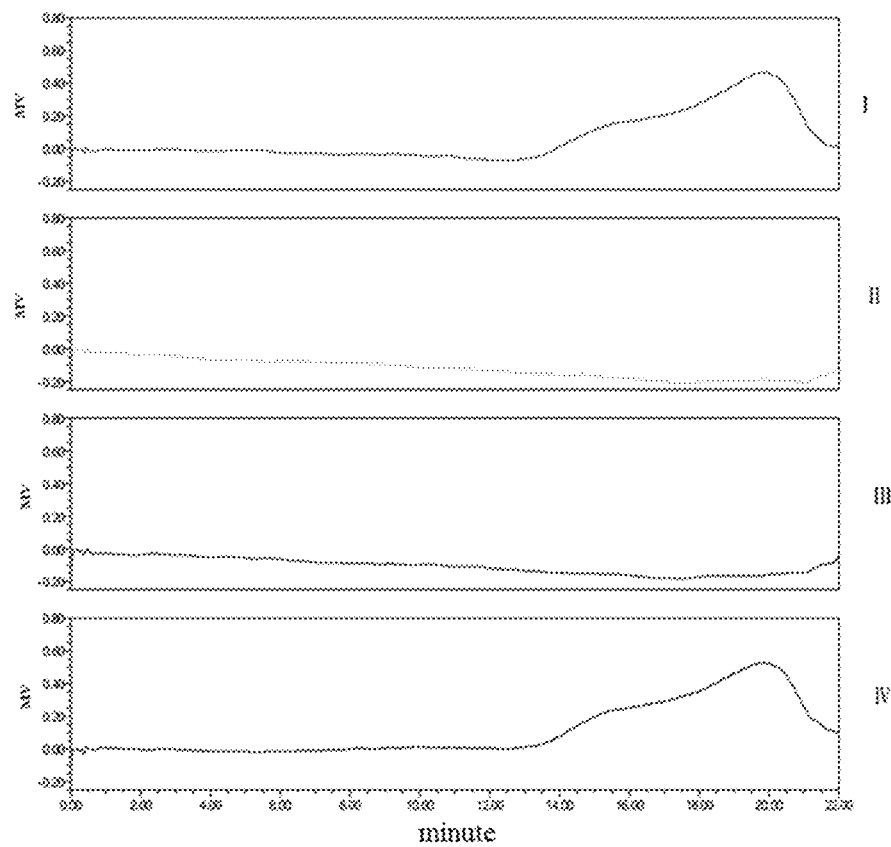
FIG. 12 shows the results of HPLC detection for protease according to an embodiment of the present disclosure, wherein, I-untreated EPS solution, II-EPS and 0.1 μM Dpo42 were incubated at 37° C., and III-EPS and 0.1 μM Dpo42 were incubated at 25° C., IV-SUMO-treated EPS solution.

As shown in FIG. 12, the untreated EPS solution showed a single peak with a retention time of 18-20 min; after incubating with Dpo42, the peak signal of polysaccharides disappeared at 18-20 min; however, the SUMO-treated EPS still showed a single peak at 18-20 min.

The activities of Dpo42 at different pH values (4.0-9.0) and different temperatures (25-80° C.) were determined using the Miller method (determination of reducing sugar with dinitrosalicylic acid reagent): glucose was used as the analytical standard, and the concentration range was 0.2-1.0 mg/mL, 500 μL standard solution and 1.5 mL DNS were added to each test tube, and boiled at 100° C. for 5 min, after cooling to room temperature, the mixture was mixed and diluted into ddH$_2$O at a ratio of 1:5 (v/v); the absorbance at 550 nm was measured using a spectrophotometer and a calibration curve was plotted.

The effect of pH on enzyme activity was determined at 37° C. under different buffer conditions: the buffer includes 50 mM sodium acetate buffer (pH=4.0-5.0), 50 mM Na$_2$HPO$_4$ buffer (pH=6.0-7.0), and 50 mM Tris –HCl buffer (pH=8.9-9.0); the effect of temperature on enzyme was studied in 50 mM Na$_2$HPO$_4$ (pH=7.0) at different temperature ranges (20-80° C.). The results are expressed as relative percentages of activity, using analysis of variance ($p<0.001$) and Dunnett pos assay for statistical analysis, * represents $p<0.05$,  represents $p<0.01$, * represents $p<0.001$, and error bar represents the standard error of mean.

Figure 13:
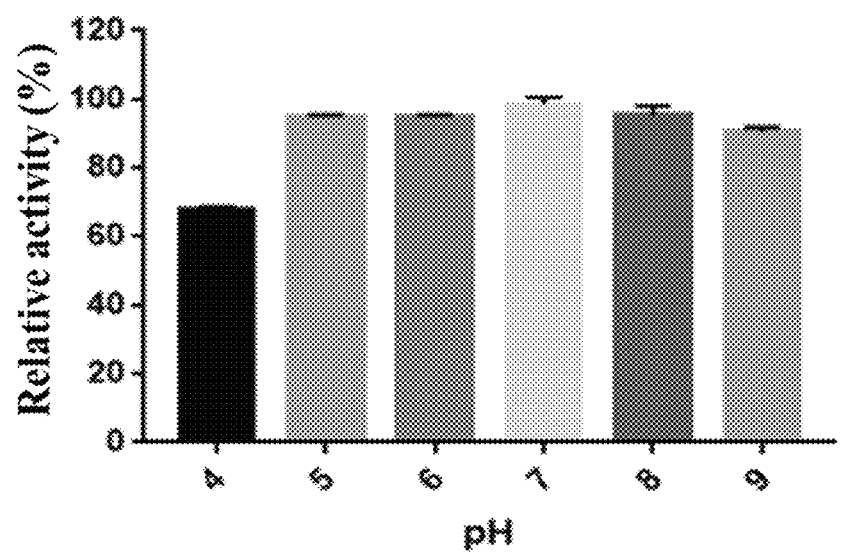
FIG. 13(A) shows the effect of pH on the enzyme activity of Dpo42 according to an embodiment of the disclosure.
FIG. 13(B) shows the effect of temperature on the enzyme activity of Dpo42 according to an embodiment of the disclosure.
Figure 13:
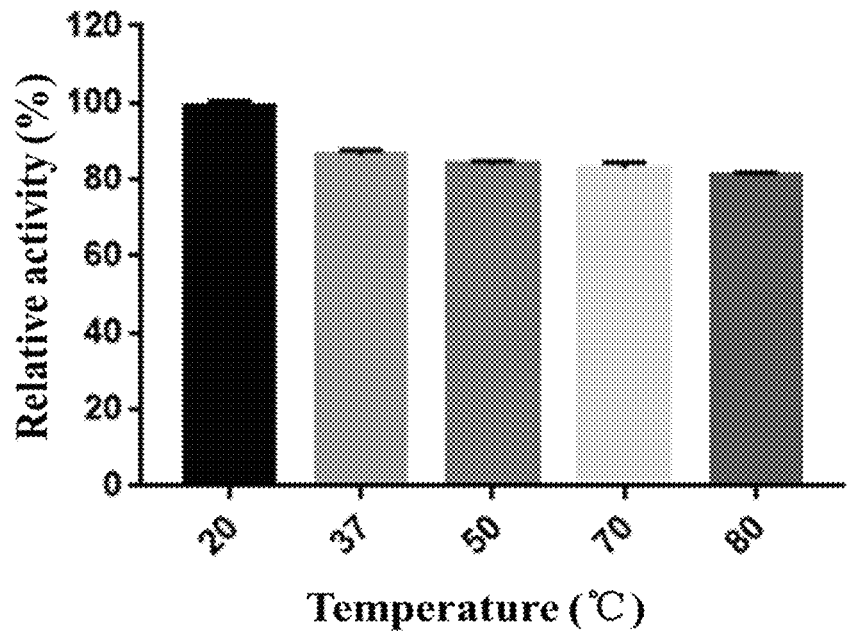

As shown in FIG. 13(A), the depolymerase Dpo42 maintained a relatively high activity in the range of pH 5.0-9.0. When the pH was 4.0, the activity decreased significantly to a relative activity of 68.06%. Since *Klebsiella pneumoniae* infects the local microenvironment at a pH of 6.5-7.0, from this perspective, in addition to antibacterial additives, polymerase is expected to become an antiviral drug candidate.

As shown in FIG. 13(B), the depolymerase Dpo42 also showed a relatively high activity in the range of 25° C.-80° C., ensuring that it has the highest efficiency in the treatment process, and functions as an antibacterial/antibacterial film retention agent.

Example 2.8 Anti-Biofilm Activity of Depolymerase

*Klebsiella pneumoniae* 2226 was used to determine the inhibitory effect of Dpo42 on biofilms:

Bacteria were cultured in fresh TSB medium until intermediate exponential stage, then 100 μL diluted sample was added into a 96-well plate, followed by recombinant depolymerase or SUMO at different concentrations (0.01 μm, 0.05 μm and 0.1 μm). The diluted bacterial culture medium and the fresh TSB medium were used as controls; after culturing at 37° C. without stirring for 72 h, the residual biofilms were determined at 595 nm by crystal violet staining assay. Analysis of variance ($p<0.001$) and Dunnett pos assay were used for the statistical analysis, * represents $p<0.05$,  represents $p<0.01$, * represents $p<0.001$, and error bar represents the standard error of mean.

Figure 14:
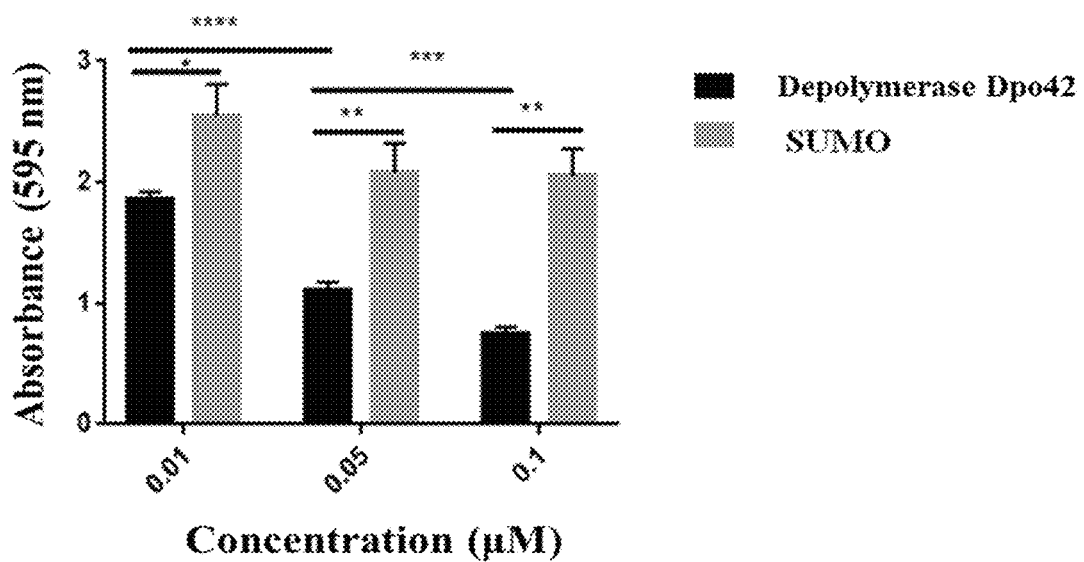
FIG. 14 shows the removal effect of different concentrations of depolymerase on *Klebsiella pneumoniae* biofilm according to an embodiment of the present disclosure.

As shown in FIG. 14, the growth of the biofilm treated with depolymerase was inhibited compared to the negative control. The OD value decreased significantly at 595 nm (P<0.05); polymerase at 0.1 μM had the strongest inhibitory effect, indicating that Dpo42 could inhibit the formation of biofilms and showed a dose-dependence during the formation of biofilms.

*Klebsiella pneumoniae* 2226 was used to determine the removal effect of Dpo42 on biofilms:

Bacteria were inoculated into a 96-well plate and grown for 48 h, the supernatant was removed, and the cells were treated with Dpo42 or SUMO at different concentrations (0.01, 0.05 and 0.1 μM) for 3 h. The diluted bacterial culture was used as a control; the crystal violet staining assay was used to evaluate the removal effect of biofilms, and A595 was determined. Analysis of variance (p<0.001) and Dunnett pos assay were used for the statistical analysis, * represents p<0.05,  represents p<0.01, * represents p<0.001, and error bar represents the standard error of mean.

Figure 15:
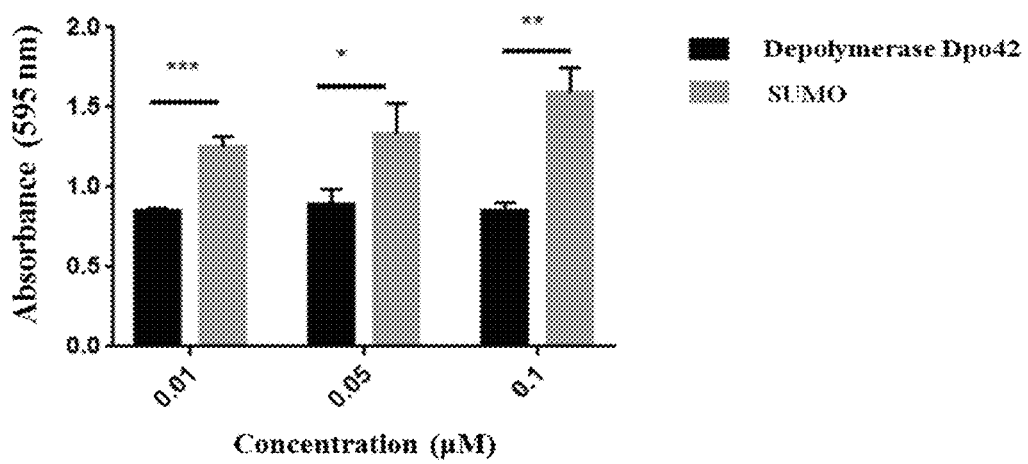
FIG. 15 shows the inhibitory effect of different concentrations of depolymerase on *Klebsiella pneumoniae* biofilm according to an embodiment of the present disclosure.

As shown in FIG. 15, the total attached biomass of biofilms decreased significantly (P<0.05) after treatment by Dpo42. Therefore, Dpo42 not only may inhibit the formation of biofilms, but also may remove biofilms.

Example 2.9 Validity Test 40 female mice (20-22 g) aged 8-10 weeks were selected and randomly divided into 5 groups, of which the mice in the four groups were intraperitoneally injected with 100 !IL of *Klebsiella pneumoniae* bacteria solution at different concentrations ($10^6$ CFU/mL, $10^7$ CFU/mL, $10^8$ CFU/mL, $10^9$ CFU/mL), and the control group was injected with the same dose of normal saline. The death of the mice was observed regularly, and the minimum dose that caused all the deaths of a group of mice was defined as the minimum lethal dose.

It was observed that the three groups of mice injected at the concentration of $10^7$ CFU/mL, $10^8$ CFU/mL and $10^9$ CFU/mL died within 24 h, while the mice injected at the concentration of $10^6$ CFU/mL only had 3 deaths within 24 h, and 5 mice survived. After 5 days, the remaining 5 mice all died. Therefore, the injection dose of $10^6$ CFU/mL *Klebsiella pneumoniae* was selected to establish a mouse model of sepsis.

40 BALB/c mice were selected and intraperitoneally injected $10^6$ CFU/mL *Klebsiella pneumoniae* to establish a mouse model of sepsis. They were randomly divided into 5 groups, and injected through the caudal vein after 2 h: the first group was injected with heat-inactivated bacteriophage Dpo42 suspension for 100 !IL/mouse, the second group was injected with normal saline for 100 μL/mouse, the third group was injected with 0.01 μM bacteriophage Dpo42 suspension for 100 μL/mouse, the fourth group was injected with 0.05 μM bacteriophage Dpo42 suspension for 100 μL/mouse, and the fifth group was injected with 0.1 μM bacteriophage Dpo42 suspension for 100 μL/mouse. The survival situation of the mice was observed daily for a total of 60 days.

Figure 16:
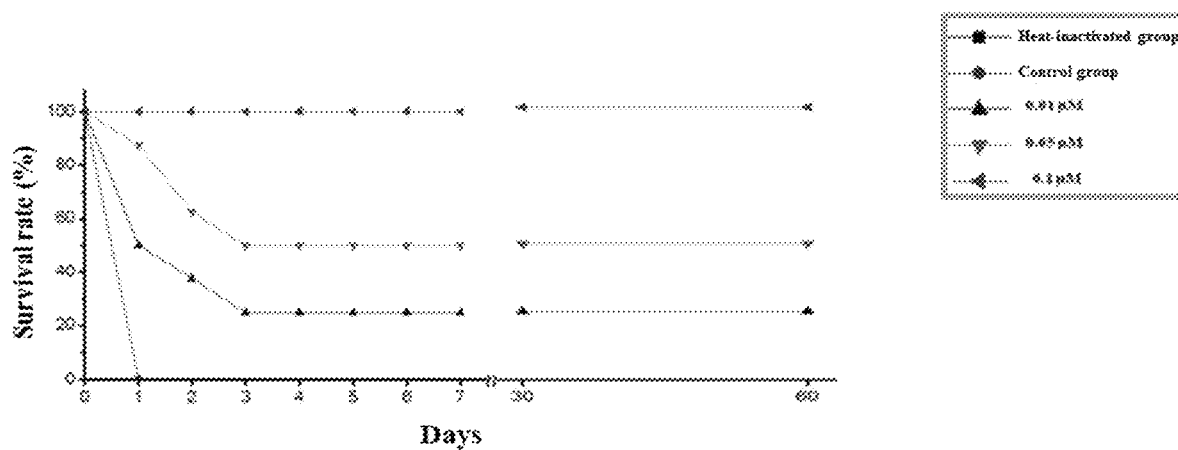
FIG. 16 is a survival curve of mice in an embodiment of the present disclosure.

The results are shown in FIG. 16. Death occurred in the mice of the third group after 1 day, and there were still 2 mice survived on the 60th day, the survival rate was 25.0%; death occurred in the mice of the fourth group after 3 days, and there were still 4 mice survived on the 60th day, the survival rate was 50.0%; all mice of the fifth group survived on the 60th day, indicating that the protection rate of bacteriophage Dpo42 with an injection dose of 0.1 μM reached 100% for mice. In addition, the mice of the first and second groups all died within 24 h, indicating that the heat-inactivated bacteriophage Dpo42 and normal saline have no protective effect for infected mice. Bacteriophage Dpo42 is confirmed to effectively treat sepsis caused by *Klebsiella pneumoniae* in mice.

Example 2.10 Safety Test

32 BALB/c mice were selected and randomly divided into 4 groups. Different concentrations (0.1 μM, 0.2 μM and 0.3 μM) of bacteriophage Dpo42 were injected intraperitoneally, respectively, with an injection dose of 100 μl/mouse, and the control group was injected with saline for 100 μl/mouse.

The results found that all mice survived normally, indicating that the high concentration (0.3 μM) of bacteriophage Dpo42 has no toxic and side effects for mice.

Each of the technical features of the above examples may be combined arbitrarily. To simplify the description, not all the possible combinations of each of the technical features in the above examples are described. However, all of the combinations of these technical features should be considered as within the scope of this disclosure, as long as such combinations do not contradict with each other.

The above-mentioned examples are merely illustrative of several embodiments of the present disclosure, which are described specifically and in detail, but it cannot be understood to limit the scope of the present disclosure. It should be noted that, for those ordinary skilled in the art, several variations and improvements may be made without departing from the concept of the present disclosure, and all of which are within the protection scope of the present disclosure. Therefore, the protection scope of the present disclosure shall be defined by the appended claims.

The invention claimed is:

1. A pharmaceutical composition, comprising:
   (i) a pharmaceutically acceptable carrier, excipient, and/or diluent;
   (ii) a depolymerase, comprising:
   (ii-a) an enzyme having a sequence as set forth in SEQ ID NO: 1; and
   (iii) an antibiotic drug having a killing or inhibitory effect on *Klebsiella pneumoniae* cells.

2. The composition of claim 1, wherein the depolymerase is derived from *Klebsiella pneumoniae* bacteriophage.

3. The composition of claim 2, wherein the *Klebsiella pneumoniae* bacteriophage is deposited with a deposit number of GDMCC No: 60968.

4. The composition of claim 1, wherein the depolymerase in (ii-a) has a depolymerase activity at pH 5 to 9 and has a depolymerase activity at 25 to 80° C.

5. A pharmaceutical composition, comprising:
   (i) a pharmaceutically acceptable carrier, excipient, and/or diluent;
   (ii) a *Klebsiella pneumoniae* bacteriophage, which is capable of expressing a depolymerase, comprising:
   (ii-a) an enzyme having a sequence as set forth in SEQ ID NO: 1; and
   (iii) an antibiotic drug having a killing or inhibitory effect on *Klebsiella pneumoniae* cells.

6. The composition of claim 5, wherein the *Klebsiella pneumoniae* bacteriophage is deposited with a deposit number of GDMCC No: 60968.

7. The composition of claim 1, wherein the antibiotic drug is one or more selected from a group consisting of: ampicillin, sulbactam, piperacillin, tazobactam, cefazolin, ceftriaxone, ceftazidime, cefepime, cefoxitin, aztreonam, ciprofloxacin, levofloxacin, gentamicin, tobramycin, amikacin, polymyxin, ertapenem, imipenem, meropenem, cotrimoxazole, and tigecycline.

8. A method of treating a disease caused by *Klebsiella pneumoniae*, the method comprising:
   administering to a host an effective amount of the pharmaceutical composition of claim 1.

9. The composition of claim 5, wherein the antibiotic drug is one or more selected from a group consisting of: ampicillin, sulbactam, piperacillin, tazobactam, cefazolin, ceftriaxone, ceftazidime, cefepime, cefoxitin, aztreonam, ciprofloxacin, levofloxacin, gentamicin, tobramycin, amikacin, polymyxin, ertapenem, imipenem, meropenem, cotrimoxazole, and tigecycline.

10. A method of treating a disease caused by *Klebsiella pneumoniae*, the method comprising:
    administering to a host an effective amount of the pharmaceutical composition of claim 5.

11. The method of claim 8, wherein the disease is a respiratory tract disease.

12. The method of claim 10, wherein the disease is a respiratory tract disease.

13. The method of claim 8, wherein the disease is a trachea infection or a lung infection.

14. The composition of claim 1, further comprising (ii-b) an enzyme having a sequence as set forth in SEQ ID NO: 2.

15. The composition of claim 5, wherein the *Klebsiella pneumoniae* bacteriophage is capable of further expressing (ii-b) an enzyme having a sequence as set forth in SEQ ID NO: 2.

16. A method of treating a disease caused by *Klebsiella pneumoniae*, the method comprising:
   administering to a host an effective amount of the pharmaceutical composition of claim 14.

17. The method of claim 16, wherein the disease is a respiratory tract disease.

18. The method of claim 16, wherein the disease is a trachea infection or a lung infection.

19. A method of treating a disease caused by *Klebsiella pneumoniae*, the method comprising:
   administering to a host an effective amount of the pharmaceutical composition of claim 15.

20. The method of claim 19, wherein the disease is a respiratory tract disease.

* * * * *

SEQUENCE LISTING

<160> NUMBER OF SEQ ID NOS: 4

<210> SEQ ID NO 1
<211> LENGTH: 793
<212> TYPE: PRT
<213> ORGANISM: Klebsiella pneumoniae bacteriophage

<400> SEQUENCE: 1

Met Asp Gln Asp Ile Lys Thr Val Ile Gln Tyr Pro Val Gly Ala Thr
1               5                   10                  15

Glu Phe Asp Ile Pro Phe Asp Tyr Leu Ser Arg Lys Phe Val Arg Val
            20                  25                  30

Ser Leu Val Ser Asp Asp Asn Arg Leu Leu Ser Asn Ile Thr Glu
                35                  40                  45

Tyr Arg Tyr Val Ser Lys Thr Arg Val Lys Leu Leu Val Glu Thr Thr
 50                  55                  60

Gly Phe Asp Arg Val Glu Ile Arg Arg Phe Thr Ser Ala Ser Glu Arg
 65                  70                  75                  80

Ile Val Asp Phe Ser Asp Gly Ser Val Leu Arg Ala Ser Asp Leu Asn
                 85                  90                  95

Val Ser Gln Ile Gln Ser Ala His Ile Ala Glu Ala Arg Asp Ala
                100                 105                 110

Ala Leu Met Ala Met Pro Gln Asp Ala Gly Asn Leu Asp Ala Arg
             115                 120                 125

Asn Arg Arg Ile Val Arg Leu Ala Pro Gly Ile Ala Gly Thr Asp Ala
130                 135                 140

Val Asn Lys Asp Gln Leu Asp Thr Thr Leu Gly Glu Ala Gly Gly Ile
145                 150                 155                 160

Leu Ser Asp Met Lys Asp Leu Glu Gly Glu Ile His Asp Tyr Ile Glu
                 165                 170                 175

Lys Phe Ala Asp Asp Thr Ala Leu Val Arg Gly Val Ala Trp Val Tyr
             180                 185                 190

Asn Leu Gly Ser Ala Asp Gly Gly Glu Thr Val Ile Thr Ile Asn Lys
             195                 200                 205

Ser Thr Arg Thr Tyr Ala Val Pro Tyr Ile Glu Val Asn Gly Ser Arg
    210                 215                 220

Gln Glu Val Gly Tyr His Tyr Ser Phe Asp Leu Glu Thr Gln Gln Ile
225                 230                 235                 240

Thr Leu Ala Thr Pro Leu Lys Ala Gly Asp Phe Val Met Val Met Thr
                245                 250                 255

Thr Glu Ser Gln Leu Pro Val Glu Thr Leu Leu Ala Ser Ser Val Gly
             260                 265                 270

Ala Ala Ser Ile Gly Thr Ala Thr Gly Glu Thr Val Glu Glu Arg Leu
         275                 280                 285

Thr Arg Leu Tyr Gly His Phe Val His Pro Glu Thr Tyr Gly Ala Val
    290                 295                 300

Gly Asp Gly Ile Thr Asp Asp Arg Val Ala Leu Gln Arg Ser Leu Asp
305                 310                 315                 320

Val Ala Tyr Glu Asn Ala Leu Asn Gly Thr Gly Pro Ser Thr Val Arg
                325                 330                 335

Trp Ser Gly Asp Tyr Met Val Ser Leu Asn Pro Asn Ser Leu Gly Val
             340                 345                 350

Ser Gly Glu Leu Ala Ala Gly Arg Ser Ala Leu Cys Ile Arg Pro Gly
         355                 360                 365

Val Ser Ile Glu Gly Lys Gly Thr Val Arg Leu Asp Pro Ser Phe Thr
    370                 375                 380

Gly Ser Gln Ser Gly Ala Val Ile Thr Asn Trp Ala Gly Pro Ala Asp
385                 390                 395                 400

Asp Cys Ser Ile Lys Asp Ile Arg Ile Tyr Gly Gly Lys Asp Val Ala
                405                 410                 415

Thr Gly Thr Gly Ile Thr Gly Ile Ile Leu Asp Ser Gln Arg Val
             420                 425                 430

Val Ile Ser Asp Val Lys Val Leu Asn Ser Thr Ala Gly Gly Ile Tyr
    435                 440                 445

Leu Arg Lys Gly Ala Thr Glu Gly Leu Tyr Gly Cys Ser Phe Ser Lys

```
                450             455             460
Val Ser Gly Cys Thr Val Asp Asn Ala Gly Tyr Ile Gly Ile Gln Met
465                 470                 475                 480

Glu Arg Pro Tyr Asp Asn Thr Val Ile Gly Asn Thr Ile Asn Arg Cys
                485                 490                 495

Glu Asp Asn Gly Ile Asp Val Phe Gly Asn Val Asn Asp Ala Thr Val
                500                 505                 510

Thr Gly Ile Ala Gln Ser Thr Leu Ile Thr Gly Asn Asn Ile Arg Asp
                515                 520                 525

Val Leu Asn Gly Val Phe Ile Glu Ser Cys Gly Asn Thr Asn Ile Thr
                530                 535                 540

Gly Asn Tyr Ile Ala Asp Phe Arg Ser Ser Gly Val Ile Tyr Asn Arg
545                 550                 555                 560

Ile Asn Ser Ala Ala Asn Asp Asn Ser Leu Thr Ser Asn Val Leu Ile
                565                 570                 575

Gly Ala Ser Gly Ala Ser Ala Gly Val Ser Phe Lys Asn Ser Val Gly
                580                 585                 590

Tyr Cys Thr Val Ala Ser Asn Arg Ile Gln Asn Ser Asp Tyr Gly Ile
                595                 600                 605

Arg Cys Val Gly Gly Ile Thr Gly Leu Asn Ile Leu Pro Asn Thr
                610                 615                 620

Met Lys Asn Ile Ala Lys Thr Leu Leu Phe Val Glu Ala Arg Asn Asn
625                 630                 635                 640

Gly Leu Val Lys Ser Arg Met Ser Thr Gln Phe Tyr Glu Gly Ala Gln
                645                 650                 655

Val Gly Gly Ile Pro Ser Asn Thr Ser Pro Arg Gly Val Pro His Arg
                660                 665                 670

Phe Pro Ser Arg Leu Ser Tyr Ile Val Asp Ile Gln Pro Phe Trp Ala
                675                 680                 685

Thr Glu Gln Gly Thr Arg Glu Asp Asn Phe Glu Arg Ala Lys Gly Thr
                690                 695                 700

Leu Ala Ser Ile Thr Gly Trp Gly Ser Lys Cys Ala Leu Tyr Asp Thr
705                 710                 715                 720

Ile Val Ala Gly Asp Thr Val Val Ser Leu Asn Ser Ser Ser Val Ala
                725                 730                 735

Val Gly Glu Tyr Leu Glu Ile Asn Ala Glu Val Tyr Lys Val Thr Ser
                740                 745                 750

Val Ser Ala Thr Tyr Ala Val Val Arg Lys Trp Thr Gly Ser Asp Tyr
                755                 760                 765

Thr Ala Gly Asp Tyr Ala Ala Val Ile Ile Ser Asn Pro Ser Tyr Ile
                770                 775                 780

Ile Arg Arg Val Gln Trp Gly Glu Gln
785                 790

<210> SEQ ID NO 2
<211> LENGTH: 641
<212> TYPE: PRT
<213> ORGANISM: Klebsiella pneumoniae bacteriophage

<400> SEQUENCE: 2

Met Leu Asn Asn Leu Asn Gln Pro Lys Gly Ser Thr Ile Gly Val Leu
1               5                   10                  15

Lys Asp Gly Arg Thr Ile Gln Gln Ala Ile Asp Gly Leu Glu Asn Pro
                20                  25                  30
```

```
Val His Tyr Val Lys Asp Val Ser Ile Thr Pro Ser Ala Leu Leu Ala
            35                  40                  45

Val Ala Val Glu Ala Ala Arg Leu Gly Arg Thr Val Glu Phe Gly Pro
 50                  55                  60

Gly His Tyr Thr Asn Gln Gly Gln Pro Phe Glu Val Asp Phe Pro Leu
 65                  70                  75                  80

Asn Leu Asp Val Pro Val Gly Thr Phe Leu Asp Phe Pro Ile Ile Ile
                85                  90                  95

Arg Gly Lys Thr Val Lys Met Val Arg Ser Val Ala Thr Asn Leu Thr
            100                 105                 110

Ala Ala Gln Cys Pro Ala Gly Thr Thr Val Ile Ala Gly Asp Phe Ser
            115                 120                 125

Ala Phe Pro Val Gly Ser Val Val Gly Val Lys Leu Gly Asp Asn Thr
 130                 135                 140

Asn Gly Ser Ala Ser Tyr Asn Asn Glu Ala Gly Trp Asp Phe Thr Thr
 145                 150                 155                 160

Val Ala Ala Ala Ser Asn Thr Ser Ile Thr Leu Ser Thr Gly Leu Arg
                165                 170                 175

Trp Ala Phe Asp Lys Pro Glu Val Phe Thr Pro Glu Tyr Ala Val Arg
            180                 185                 190

Tyr Ser Gly Gln Leu Ser Arg Ser Ser Tyr Phe Ile Pro Gly Asp Tyr
            195                 200                 205

Thr Ser Gly Leu Asn Val Gly Asp Ile Ile Arg Val Glu Asn Ile Asp
 210                 215                 220

Gly Thr Asp Gly Val His Gly Asn Lys Glu Tyr Phe Glu Met Leu Lys
225                 230                 235                 240

Val Ser Ser Ile Asp Ser Ser Gly Ile Thr Val Glu Thr Arg Leu Arg
                245                 250                 255

Tyr Thr His Val Asn Pro Trp Ile Val Lys Thr Gly Leu Val Lys Gly
            260                 265                 270

Ser Ser Val Thr Gly Gly Arg Leu Lys Arg Leu Glu Val Arg Gly
            275                 280                 285

Val Asp Thr Pro Lys Val Asn Asn Val Asp Val Asp Arg Leu Ile Val
 290                 295                 300

Gly Leu Cys Tyr Asn Ile Asp Val Gly Glu Ile Thr Ser Arg Gly Val
305                 310                 315                 320

Gly Glu Pro Ser Ser Val Asn Phe Thr Phe Cys Phe Gly Arg Gly Phe
                325                 330                 335

Leu Tyr Asn Val Arg Ala Ser Gly Ser Val Ser Thr Thr Asp Asn Ser
            340                 345                 350

Ala Leu Lys Leu Met Ser Cys Pro Gly Leu Ile Ile Asn Asn Cys Ser
            355                 360                 365

Pro His Asn Ser Thr Ser Thr Gly Ser Gln Gly Asp Tyr Gly Phe Tyr
 370                 375                 380

Val Asp Ala Tyr Tyr Pro Pro Tyr Trp Cys Trp Asn Asp Gly Met Ser
385                 390                 395                 400

Ile Asn Gly Ile Val Thr Glu Thr Pro Arg Ser Ala Val Thr Arg Ala
                405                 410                 415

Leu Trp Leu Phe Gly Leu Arg Gly Cys Ser Val Ser Asn Leu Ser Gly
            420                 425                 430

Ala Gln Val Phe Leu Gln Gly Cys Ala Lys Ser Val Phe Ser Asn Ile
            435                 440                 445

Val Thr Pro Asp Asn Leu Leu Glu Leu Arg Asp Leu Ser Gly Cys Ile
```

```
                    450             455             460
Val Ser Gly Met Ala Asn Asn Ala Leu Val Leu Gly Cys Trp Asn Ser
465                 470                 475                 480

Thr Phe Asp Leu Thr Leu Phe Gly Ile Gly Ser Gly Ser Asn Leu Asn
                485                 490                 495

Ile Ala Leu Arg Ala Gly Ala Gly Val Thr His Pro Glu Thr Gly Val
                500                 505                 510

Pro Thr Thr Leu Gly Lys Asn Asn Thr Phe Asn Val Lys Ser Phe Ser
            515                 520                 525

Pro Ser Ser Leu Ala Val Thr Leu Ser Ile Ala Gln Gln Glu Arg Pro
            530                 535                 540

Ile Phe Gly Ala Gly Cys Val Asp Val Asp Ser Ala Asn Lys Ser Val
545                 550                 555                 560

Thr Leu Gly Ser Asn Val Thr Val Pro Thr Met Leu Pro Leu Ala Leu
                565                 570                 575

Thr Lys Gly Ile Asp Ser Gly Ser Gly Trp Val Gly Gly Arg Thr Lys
                580                 585                 590

Gly Gly Ile Trp Phe Asp Gly Asn Tyr Arg Asp Ala Ala Val Arg Trp
                595                 600                 605

Asn Gly Gln Tyr Val Trp Val Ala Asp Asn Gly Ser Leu Lys Ala Ala
                610                 615                 620

Pro Thr Lys Pro Asp Ser Asp Ser Pro Ser Asn Gly Val Val Ile Gly
625                 630                 635                 640

Pro

<210> SEQ ID NO 3
<211> LENGTH: 2382
<212> TYPE: DNA
<213> ORGANISM: Klebsiella pneumoniae bacteriophage

<400> SEQUENCE: 3
atggaccaag acattaaaac agtcattcag tacccagtag gggccactga gttcgacatc      60
ccgttcgact acctgtcccg taagtttgtc cgtgtgtcgc tggtgtcaga cgataaccgc     120
agactgctaa gtaacatcac tgagtaccgc tacgtgtcta agaccagagt gaagctcctt     180
gtggaaacta ccgggttcga ccgtgtggaa atccgcaggt tcacctcggc gtctgagcga     240
atcgttgact tcagcgatgg ctcggttctc cgcgcttctg accttaacgt atctcaaata     300
cagtcggcgc atatcgcaga ggaagcacgt gacgcggcac tcatggccat gccacaggat     360
gacgctggga accttgatgc gcgcaaccgt agaatcgtaa ggttggcacc gggtattgcc     420
gggacggatg cagtgaacaa ggaccagctt gacacgacct aggagaggc tggtggtatc     480 ctatcggaca tgaaggacct agagggtgag attcatgact acatcgagaa gtttgcagat     540
gacactgcgc ttgtgcgtgg ggtggcgtgg gtgtataacc ttggttccgc tgatggtggg     600
gaaaccgtta tcaccataaa taaatcgaca cgtacatacg ctgtgcctta cattgaggta     660
aatggctcac gccaagaggt cgggtatcac tattcgttcg atctggaaac acagcagata     720
acccttgcca ccccattgaa agctggcgac ttcgttatgg taatgaccac agagtctcag     780
ctcccggtag agacattgct ggcatctagc gttggtgccg cgagcatcgg gacggccaca     840
ggagagacag ttgaggagcg acttactcga ctttacgggc actttgtgca ccctgagacg     900
tatggtgctg taggtgatgg cataacagac gaccgagttg cactccagcg ctcactagat     960
gtggcttatg agaatgcgct gaatggtact ggcccgtcga ctgtacgctg gtcaggagac    1020
```

-continued

| | |
|---|---|
| tacatggtgt cgctgaaccc taactcatta ggcgtttctg gggaactggc agcaggccgc | 1080 |
| tcagcactat gtatccgacc cggtgtgtca attgaaggta agggcacggt ccgtcttgac | 1140 |
| ccatccttta caggaagcca gtctggcgca gtaataacca actgggctgg tccagctgac | 1200 |
| gactgctcca ttaaggatat acggatttac ggcggtaagg acgtagccac tggtactggc | 1260 |
| ataaccggaa tccttattct ggattcacag agagtagtca tatctgacgt taaggttctg | 1320 |
| aacagtacag ctggtggtat ctatctgaga aaggtgccca cagagggtct gtatggatgc | 1380 |
| tcattcagca aggtctcagg gtgtactgtg ataacgctg ggtacattgg aatccagatg | 1440 |
| gagagaccat acgataatac cgtcattgga aacacaatca atcggtgtga agataacggc | 1500 |
| attgacgtgt tcggtaacgt aaacgatgct acggtaacgg gcattgcgca atccacgcta | 1560 |
| atcactggca acaacataag ggatgtccta acggagtgt tcattgaatc ctgcggcaac | 1620 |
| acaaacatta ccggaaacta catcgcggac tttcgctcca gcggggtcat ctacaaccgc | 1680 |
| atcaactcgg cggcaaatga taactcactc acctcaaacg tactcatcgg cgcctcaggt | 1740 |
| gcttcggcag gtgttagctt caagaactca gtaggatact gtacagtggc gagcaacagg | 1800 |
| attcagaata gtgactacgg gattcgatgc gttggcggag gcattaccgg gcttaacatc | 1860 |
| ctcccaaata cgatgaagaa catcgctaag accctgctgt tgtggaggc ccgtaacaac | 1920 |
| ggtctggtca agtcacgtat gtctacccag ttctacgagg gggcacaggt cggcgggatt | 1980 |
| ccgagtaaca cctctccaag aggagtaccg cacagattcc catcaaggct ctcttatatt | 2040 |
| gtggatatcc aaccgttctg ggcaacagag cagggtaccc gcgaggataa cttcgagaga | 2100 |
| gcaaaaggga ccttggcgtc aatcactggg tggggttcaa agtgtgccct gtatgacacg | 2160 |
| attgtggcag gtgatacggt ggtgtctctt aactcatcgt cagtagctgt gggcgaatac | 2220 |
| cttgagatta acgcggaggt ttataaggtt actagcgtat ccgcaactta cgccgtggtt | 2280 |
| cgaaaatgga ctggttcgga ttacacggct ggagactacg cagcggtaat tattagtaat | 2340 |
| ccatcctaca tcattcgccg ggtgcagtgg ggcgaacagt aa | 2382 |

<210> SEQ ID NO 4
<211> LENGTH: 1926
<212> TYPE: DNA
<213> ORGANISM: Klebsiella pneumoniae bacteriophage

<400> SEQUENCE: 4

| | |
|---|---|
| atgttaaaca acctgaacca gccgaaaggc tcaaccattg gtgtgctcaa ggatgggcgc | 60 |
| actatccaac aggcaattga tggcttggag aacccggtgc attacgtcaa agatgtgagc | 120 |
| atcacgccat cggcactact ggcagtagcg gtagaggctg cacgacttgg ccggactgtg | 180 |
| gagtttgggc cgggtcacta cacgaaccaa ggtcagccat cgaggtgga cttcccgctt | 240 |
| aatctggatg ttccagtagg aacctttctg gacttcccta tcatcatacg aggtaagacc | 300 |
| gtgaagatgg tcaggagtgt ggccacgaac cttactgccg cccagtgccc tgctggtaca | 360 |
| acagtcatcg ccggggactt ctcagcgttc cctgttggtt ccgtcgtggg tgtaaaactt | 420 |
| ggggataata ccaacggctc agcaagttat aacaacgagg ctggctggga tttcactaca | 480 |
| gtcgcggcgg cgtccaacac ctcaatcacc ctcagcacag gctacggtg gctttcgat | 540 |
| aaaccggaag tgtttacccc ggagtatgcg gtacgatact caggacagct gagtcggtca | 600 |
| tcttacttca taccgggaga ttacacttcc gggctgaatg ttggagatat catccgtgtt | 660 |
| gagaacatta tggtactga cggggtccac ggcaacaagg aatacttcga gatgcttaag | 720 |
| gtatcaagta tagattcctc aggtataaca gttgagacgc gccttcggta tacccatgtg | 780 |

```
aacccttgga ttgtaaagac agggctggtc aaaggctctt cggtaaccgg gggggccga      840 ttgaagcgtt tagaagtacg cggtgtcgac acgccaaagg ttaacaatgt agatgtggac      900
cgcttaattg tcggcctgtg ctacaacatc gacgttgggg agataacctc tcgtggcgtt      960
ggtgagcctt cctcggtgaa cttcacgttc tgcttcggtc gtggcttcct gtacaacgta     1020
agggcctctg ggtcagtgtc cacaacggat aactcagcgt taaagctgat gagctgtccc     1080
ggcctaatca ttaacaactg ttcacctcac aactctacat ccactggttc tcaaggtgac     1140
tacgggttct acgttgacgc ctattaccct ccgtactggt gctggaacga cggcatgtcc     1200
atcaatggga ttgtcactga gacacctagg tcggctgtaa cgcgtgcgct gtggctgttt     1260
ggtctgagag gctgttctgt tagtaacctg tccggtgccc aagtgttcct acagggctgc     1320
gctaagtcgg tgttctccaa catcgtcacc ccggacaatc tccttgaact acgggacctt     1380
tctggctgca ttgtatccgg catggcaaat aacgcgctgg tactcggctg ttggaactcg     1440
acgttcgacc ttacgctatt tggtattggc tctgggtcaa accttaacat agcgttacgg     1500 gcagggcag gcgttaccca cccggagact ggtgtgccca ctaccctcgg taagaacaac      1560
acgttcaacg ttaagagttt tagcccatcg tcgcttgctg tcaccctaag tatcgcccag     1620
caagagcgcc caatcttcgg tgctggctgt gttgacgtcg attctgcaaa caagtcagtc     1680
actctcggta gtaacgttac cgtcccgacc atgctcccgc tggcgttaac caaaggtatc     1740
gactccggct ctggctgggt tggtggaagg actaaggggtg gtatctggtt cgatggtaac    1800
taccgcgatg cggcggtgcg ctggaacggc cagtacgtat gggtggctga caatggttcg     1860
ctcaaagcag cgcctactaa accggattct gactcgcctt ccaatggtgt ggttatcggt     1920
ccataa                                                                1926
```